US011741619B2

(12) United States Patent
Aghdasi et al.

(10) Patent No.: US 11,741,619 B2
(45) Date of Patent: Aug. 29, 2023

(54) METHODS AND SYSTEMS FOR REGISTERING PREOPERATIVE IMAGE DATA TO INTRAOPERATIVE IMAGE DATA OF A SCENE, SUCH AS A SURGICAL SCENE

(71) Applicant: Proprio, Inc., Seattle, WA (US)

(72) Inventors: Nava Aghdasi, Kirkland, WA (US); James Andrew Youngquist, Seattle, WA (US)

(73) Assignee: Propio, Inc., Seattle, WA (US)

( * ) Notice: Subject to any disclaimer, the term of this patent is extended or adjusted under 35 U.S.C. 154(b) by 244 days.

(21) Appl. No.: 17/141,482

(22) Filed: Jan. 5, 2021

(65) Prior Publication Data

US 2022/0215532 A1 Jul. 7, 2022

Related U.S. Application Data

(63) Continuation of application No. 17/140,885, filed on Jan. 4, 2021, now Pat. No. 11,295,460.

(51) Int. Cl.
*G06K 9/00* (2022.01)
*G06T 7/30* (2017.01)
(Continued)

(52) U.S. Cl.
CPC ............ *G06T 7/30* (2017.01); *G06T 5/009* (2013.01); *G06T 7/0012* (2013.01); *G06T 7/38* (2017.01);
(Continued)

(58) Field of Classification Search
CPC .................................................... G06T 7/30
See application file for complete search history.

(56) References Cited

U.S. PATENT DOCUMENTS

| 6,167,296 A | 12/2000 | Shahidi |
| 6,675,040 B1 | 1/2004 | Cosman |

(Continued)

FOREIGN PATENT DOCUMENTS

| EP | 1504713 B1 | 7/2008 |
| EP | 2139419 A1 | 1/2010 |

(Continued)

OTHER PUBLICATIONS

PCT International Search Report and Written Opinion, PCT Application No. PCT/US20/14674, dated Apr. 21, 2020, 6 pages.

(Continued)

*Primary Examiner* — Oneal R Mistry
(74) *Attorney, Agent, or Firm* — Perkins Coie LLP

(57) ABSTRACT

Mediated-reality imaging systems, methods, and devices are disclosed herein. In some embodiments, an imaging system includes (i) a camera array configured to capture intraoperative image data of a surgical scene in substantially real-time and (ii) a processing device communicatively coupled to the camera array. The processing device can be configured to synthesize a three-dimensional (3D) image corresponding to a virtual perspective of the scene based on the intraoperative image data from the cameras. The imaging system is further configured to receive and/or store preoperative image data, such as medical scan data corresponding to a portion of a patient in the scene. The processing device can register the preoperative image data to the intraoperative image data, and overlay the registered preoperative image data over the corresponding portion of the 3D image of the scene to present a mediated-reality view.

16 Claims, 18 Drawing Sheets

(51) Int. Cl.
*G06T 19/20* (2011.01)
*G06T 19/00* (2011.01)
*G06T 7/38* (2017.01)
*G06T 7/00* (2017.01)
*G06T 5/00* (2006.01)
*H04N 23/90* (2023.01)

(52) U.S. Cl.
CPC .............. *G06T 7/97* (2017.01); *G06T 19/006* (2013.01); *G06T 19/20* (2013.01); *H04N 23/90* (2023.01); *G06T 2207/10081* (2013.01); *G06T 2207/30008* (2013.01); *G06T 2207/30012* (2013.01); *G06T 2219/2016* (2013.01)

(56) References Cited

U.S. PATENT DOCUMENTS

| | | | |
|---|---|---|---|
| 6,985,765 B2 | 1/2006 | Morita et al. | |
| 7,844,320 B2 | 11/2010 | Shahidi | |
| 8,010,177 B2 | 8/2011 | Csavoy et al. | |
| 8,041,089 B2 | 10/2011 | Drumm et al. | |
| 8,295,909 B2 | 10/2012 | Goldbach | |
| 8,548,563 B2 | 10/2013 | Simon et al. | |
| 8,657,809 B2 | 2/2014 | Schoepp | |
| 8,933,935 B2 | 1/2015 | Yang et al. | |
| 9,119,670 B2 | 9/2015 | Yang et al. | |
| 9,314,219 B2 | 4/2016 | Keall et al. | |
| 9,916,691 B2 | 3/2018 | Takano et al. | |
| 9,968,408 B1 | 5/2018 | Casey et al. | |
| 10,013,777 B2 | 7/2018 | Mariampillai et al. | |
| 10,022,065 B2 | 7/2018 | Ben-yishai et al. | |
| 10,074,177 B2 | 9/2018 | Piron et al. | |
| 10,165,981 B2 | 1/2019 | Schoepp | |
| 10,166,078 B2 | 1/2019 | Sela et al. | |
| 10,166,079 B2 | 1/2019 | Mclachlin et al. | |
| 10,194,131 B2 | 1/2019 | Casas | |
| 10,390,887 B2 | 8/2019 | Bischoff et al. | |
| 10,398,514 B2 | 9/2019 | Ryan et al. | |
| 10,424,118 B2 | 9/2019 | Hannemann et al. | |
| 10,426,554 B2 | 10/2019 | Siewerdsen et al. | |
| 10,455,218 B2 | 10/2019 | Venkataraman et al. | |
| 10,463,434 B2 | 11/2019 | Siegler et al. | |
| 10,482,614 B2 | 11/2019 | Ben-yishai | |
| 10,546,423 B2 | 1/2020 | Jones et al. | |
| 10,575,906 B2 | 3/2020 | Wu | |
| 10,650,573 B2 | 5/2020 | Youngquist et al. | |
| 10,653,495 B2 | 5/2020 | Gregerson et al. | |
| 10,667,868 B2 | 6/2020 | Malackowski | |
| 10,682,188 B2 | 6/2020 | Leung et al. | |
| 10,709,509 B2 | 7/2020 | Scholl et al. | |
| 10,792,110 B2 | 10/2020 | Leung et al. | |
| 10,799,315 B2 | 10/2020 | Leung et al. | |
| 10,799,316 B2 | 10/2020 | Sela et al. | |
| 10,810,799 B2 | 10/2020 | Tepper et al. | |
| 10,828,114 B2 | 11/2020 | Abhari et al. | |
| 10,832,408 B2 | 11/2020 | Srimohanarajah et al. | |
| 10,912,625 B2 | 2/2021 | Browd et al. | |
| 10,918,444 B2 | 2/2021 | Stopp et al. | |
| 10,949,986 B1 | 3/2021 | Colmenares et al. | |
| 11,042,989 B2 | 6/2021 | Linguraru et al. | |
| 2003/0210812 A1 | 11/2003 | Khamene et al. | |
| 2004/0097805 A1* | 5/2004 | Verard ................ | A61B 8/4254 600/428 |
| 2004/0169673 A1 | 9/2004 | Crampe et al. | |
| 2004/0215071 A1* | 10/2004 | Frank .................... | A61B 6/463 600/407 |
| 2005/0070789 A1 | 3/2005 | Aferzon | |
| 2006/0036156 A1 | 2/2006 | Lachaine et al. | |
| 2008/0071140 A1 | 3/2008 | Gattani et al. | |
| 2010/0099981 A1 | 4/2010 | Fishel | |
| 2011/0098553 A1 | 4/2011 | Robbins et al. | |
| 2014/0044333 A1* | 2/2014 | Barth, Jr. .................. | G06T 7/33 382/131 |
| 2016/0063821 A1 | 3/2016 | Macintosh et al. | |
| 2016/0191887 A1 | 6/2016 | Casas | |
| 2016/0217576 A1 | 7/2016 | Kabus et al. | |
| 2016/0354161 A1 | 12/2016 | Deitz | |
| 2017/0084036 A1 | 3/2017 | Pheiffer et al. | |
| 2017/0099479 A1 | 4/2017 | Browd et al. | |
| 2017/0165008 A1* | 6/2017 | Finley .................. | A61B 6/5235 |
| 2017/0178349 A1* | 6/2017 | Ketcha .................... | G06T 7/33 |
| 2017/0202626 A1 | 7/2017 | Kula et al. | |
| 2017/0296293 A1 | 10/2017 | Mak et al. | |
| 2017/0323062 A1 | 11/2017 | Djajadiningrat et al. | |
| 2018/0078316 A1 | 3/2018 | Schaewe et al. | |
| 2019/0038362 A1 | 2/2019 | Nash et al. | |
| 2019/0046269 A1* | 2/2019 | Hedblom .................. | G06T 7/62 |
| 2019/0088360 A1 | 3/2019 | Goble et al. | |
| 2019/0209080 A1 | 7/2019 | Gullotti et al. | |
| 2019/0289284 A1* | 9/2019 | Smith .................. | H04N 13/282 |
| 2019/0290366 A1 | 9/2019 | Pettersson et al. | |
| 2019/0311805 A1 | 10/2019 | Linguraru et al. | |
| 2019/0320995 A1* | 10/2019 | Amiri .................... | A61B 34/00 |
| 2019/0328465 A1 | 10/2019 | Li et al. | |
| 2019/0350657 A1* | 11/2019 | Tolkowsky ............. | A61B 46/20 |
| 2019/0350658 A1 | 11/2019 | Yang et al. | |
| 2020/0105065 A1 | 4/2020 | Youngquist et al. | |
| 2020/0197100 A1 | 6/2020 | Leung et al. | |
| 2020/0197102 A1 | 6/2020 | Shekhar et al. | |
| 2020/0229893 A1 | 7/2020 | Browd et al. | |
| 2020/0297427 A1 | 9/2020 | Cameron et al. | |
| 2020/0352651 A1 | 11/2020 | Junio et al. | |
| 2020/0375689 A1 | 12/2020 | Browd et al. | |
| 2020/0405395 A1* | 12/2020 | Gullotti .............. | A61B 17/7082 |
| 2020/0405399 A1* | 12/2020 | Steinberg ............... | G06N 20/00 |
| 2020/0405433 A1 | 12/2020 | Sela et al. | |
| 2021/0038340 A1 | 2/2021 | Itkowitz et al. | |
| 2021/0045618 A1 | 2/2021 | Stricko et al. | |
| 2021/0045813 A1 | 2/2021 | Wickham et al. | |
| 2021/0145517 A1 | 5/2021 | Pierrepont et al. | |
| 2021/0177526 A1* | 6/2021 | Goyette .................. | A61B 34/20 |
| 2021/0186355 A1 | 6/2021 | Ben-yishai et al. | |
| 2021/0192763 A1 | 6/2021 | Liu et al. | |
| 2021/0196385 A1 | 7/2021 | Shelton et al. | |
| 2021/0287454 A1 | 9/2021 | Shah | |
| 2021/0307863 A1 | 10/2021 | Ben-yishai | |

FOREIGN PATENT DOCUMENTS

| | | | | |
|---|---|---|---|---|
| EP | 1924197 | B1 | 10/2017 | |
| EP | 3197382 | A4 | 6/2018 | |
| EP | 2852326 | B1 | 12/2018 | |
| EP | 3102141 | B1 | 8/2019 | |
| WO | 2007115825 | A1 | 10/2007 | |
| WO | 2008130354 | A1 | 10/2008 | |
| WO | 2010067267 | A1 | 6/2010 | |
| WO | 2017042171 | A1 | 3/2017 | |
| WO | 2018097831 | A1 | 5/2018 | |
| WO | 2019010203 | A1 | 1/2019 | |
| WO | WO-2019010203 | A1 * | 1/2019 | ......... A61B 17/7032 |
| WO | 2020154448 | A1 | 7/2020 | |
| WO | 2020163316 | A1 | 8/2020 | |
| WO | 2021003401 | A1 | 1/2021 | |
| WO | 2021070188 | A1 | 4/2021 | |

OTHER PUBLICATIONS

International Search Report and Written Opinion received in Application No. PCT/US21/65460, dated May 4, 2022, 21 pages.

\* cited by examiner

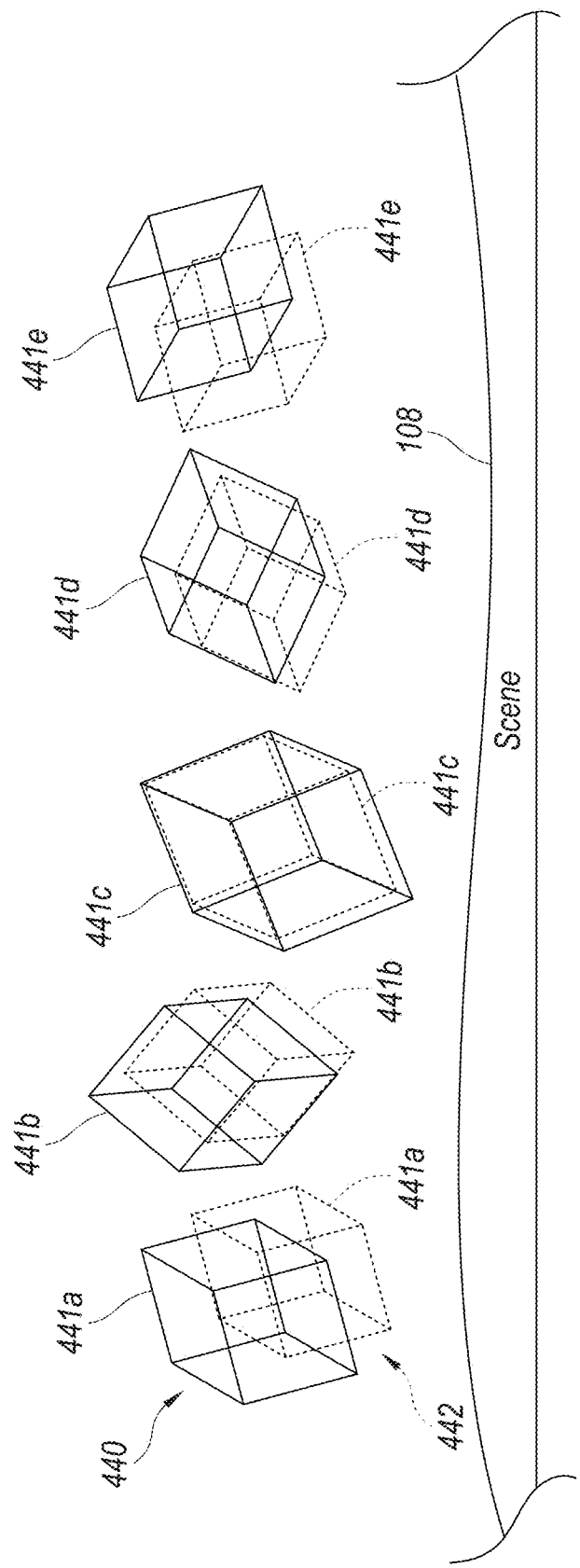

METHODS AND SYSTEMS FOR REGISTERING PREOPERATIVE IMAGE DATA TO INTRAOPERATIVE IMAGE DATA OF A SCENE, SUCH AS A SURGICAL SCENE

CROSS-REFERENCE TO RELATED APPLICATION(S)

This application is a continuation of U.S. patent application Ser. No. 17/140,885, filed Jan. 4, 2021, and titled "METHODS AND SYSTEMS FOR REGISTERING PREOPERATIVE IMAGE DATA TO INTRAOPERATIVE IMAGE DATA OF A SCENE, SUCH AS A SURGICAL SCENE," the disclosure of which is incorporated herein in its entirety.

TECHNICAL FIELD

The present technology generally relates to methods and systems for generating a real-time or near-real-time three-dimensional (3D) virtual perspective of a scene for a mediated-reality viewer, and registering previously-captured image data, such as preoperative medical images (e.g., computed tomography (CT) scan data), to the 3D virtual perspective.

BACKGROUND

In a mediated reality system, an image processing system adds, subtracts, and/or modifies visual information representing an environment. For surgical applications, a mediated reality system may enable a surgeon to view a surgical site from a desired perspective together with contextual information that assists the surgeon in more efficiently and precisely performing surgical tasks. When performing surgeries, surgeons often rely on preoperative three-dimensional images of the patient's anatomy, such as computed tomography (CT) scan images. However, the usefulness of such preoperative images is limited because the images cannot be easily integrated into the operative procedure. For example, because the images are captured in a preoperative session, the relative anatomical positions captured in the preoperative images may vary from their actual positions during the operative procedure. Furthermore, to make use of the preoperative images during the surgery, the surgeon must divide their attention between the surgical field and a display of the preoperative images. Navigating between different layers of the preoperative images may also require significant attention that takes away from the surgeon's focus on the operation.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

FIGS. 4A-4C are schematic illustrations of (i) intraoperative image data of an object within the field of view of a camera array of the imaging system of FIG. 1 and (ii) preoperative image data of the object, and illustrating various stages of the method of FIG. 3 in accordance with embodiments of the present technology.

DETAILED DESCRIPTION

Figure 1:
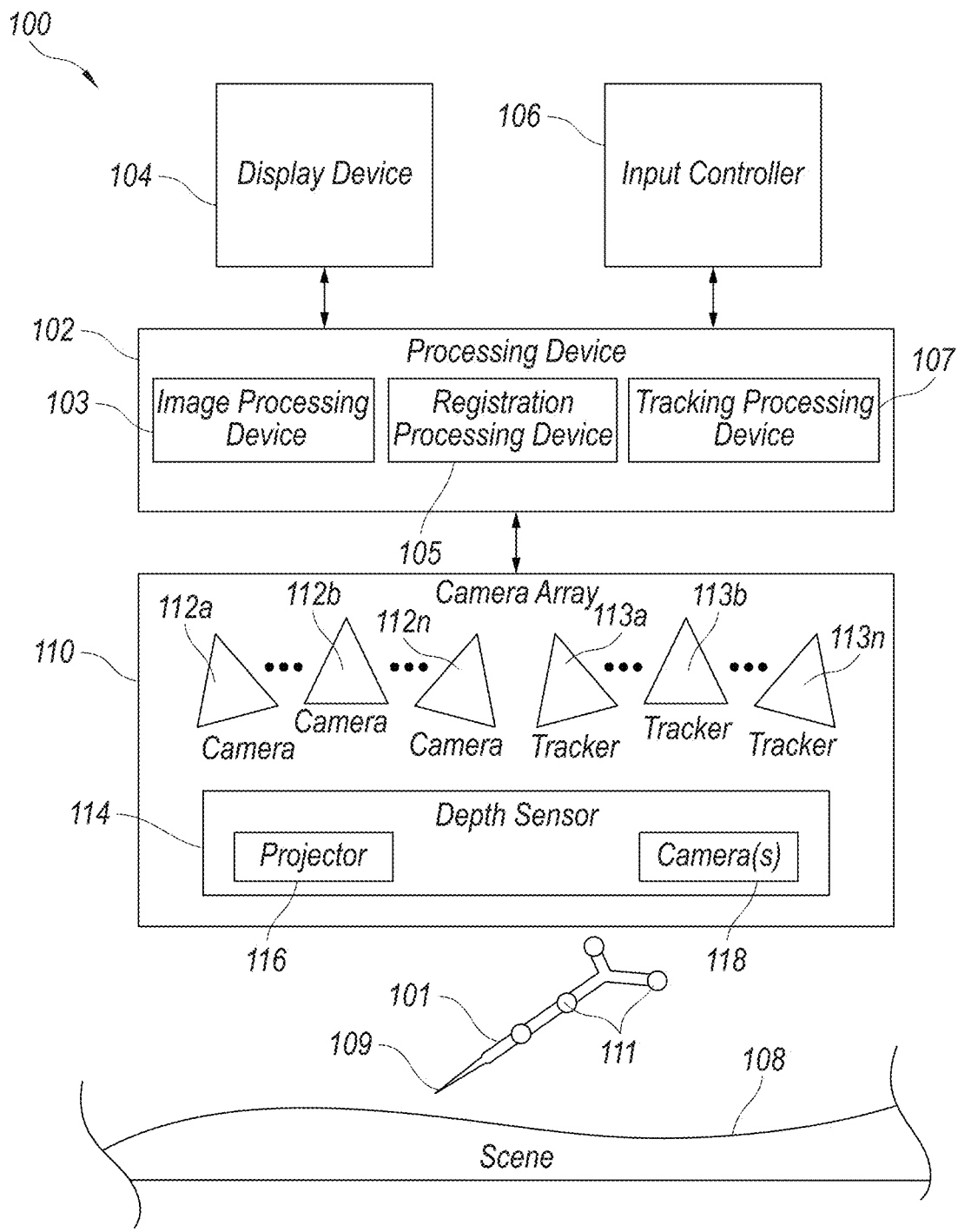
FIG. 1 is a schematic view of an imaging system in accordance with embodiments of the present technology.

Aspects of the present technology are directed generally to mediated-reality imaging systems, such as for use in surgical procedures, and associated methods for registering preoperative image data to intraoperative image data for display together. In several of the embodiments described below, for example, an imaging system includes (i) a camera array configured to capture intraoperative image data (e.g., light-field data and/or depth data) of a surgical scene and (ii) a processing device communicatively coupled to the camera array. The processing device can be configured to synthesize/generate a three-dimensional (3D) virtual image corresponding to a virtual perspective of the scene in real-time or near-real-time based on the image data from at least a subset of the cameras. The processing device can output the 3D virtual image to a display device (e.g., a head-mounted display (HMD)) for viewing by a viewer, such as surgeon or other operator of the imaging system. The imaging system is further configured to receive and/or store preoperative image data. The preoperative image data can be medical scan data (e.g., computerized tomography (CT) scan data) corresponding to a portion of a patient in the scene, such as a spine of a patient undergoing a spinal surgical procedure.

The processing device can globally and/or locally register the preoperative image data to the intraoperative image data by, for example, registering/matching fiducial markers and/or other feature points visible in 3D data sets representing both the preoperative and interoperative image data. The processing device can further apply a transform to the preoperative image data based on the registration to, for example, substantially align (e.g., in a common coordinate frame) the preoperative image data with the real-time or near-real-time intraoperative image data captured with the camera array. The processing device can then display the preoperative image data and the intraoperative image data together to provide a mediated-reality view of the surgical scene. More specifically, the processing device can overlay a 3D graphical representation of the preoperative image data over a corresponding portion of the 3D virtual image of the scene to present the mediated-reality view that enables, for example, a surgeon to simultaneously view a surgical site in the scene and the underlying 3D anatomy of the patient undergoing the operation.

In some embodiments, the processing device of the imaging system can implement a method for registering the preoperative image data, such as medical scan data, to the intraoperative image data that includes overlaying the unregistered medical scan data over the 3D virtual image. The method can further include receiving a user input to move the medical scan data into alignment with a corresponding portion of the patient at least partially visible in the 3D virtual image (e.g., a selected anatomy of the patient). For example, the medical scan data can be a segmented vertebra from a CT scan, and the user can virtually "drag and drop" the vertebra into alignment with the corresponding vertebra shown in the 3D virtual image by moving a tool through the scene. Once the medical scan data has been manually aligned by the user, the method can include registering the medical scan data to the intraoperative image based on the alignment. In some embodiments, the registration can be a local registration that further aligns the medical scan data to the intraoperative image data. Such a local registration can be visibly represented in the 3D virtual image by "snapping" the medical scan data into position over the corresponding anatomy of the patient in the 3D virtual image.

In some embodiments, the processing device of the imaging system can implement a method for registering the preoperative medical scan data to the intraoperative image data that is based on one or more characteristics of the intraoperative image data, such as color, specularity, and the like. More specifically, the method can include analyzing intraoperative light-field image data to determine the one or more characteristics and, based on the determined one or more characteristics, determining that (i) a first portion of the intraoperative image data corresponds to a first type of anatomy the patient and (ii) a second portion of the intraoperative image data corresponds to a second type of anatomy of the patient. The first type of anatomy can correspond to the medical scan data. For example, the medical scan data can be a CT scan of a spine of the patient, and the first type of anatomy of the patient can be spinal bone. In some embodiments, the method can include adjusting the weights of a registration algorithm based on whether points in the intraoperative image data are of the first type of anatomy or the second type of anatomy. For example, points that are likely bone can be weighted higher than points that are likely flesh or other anatomy of the patient that does not correspond to the medical scan data.

In some embodiments, the processing device of the imaging system can implement a method for registering the preoperative medical scan data to the intraoperative image data that includes processing intraoperative depth data of the scene. More specifically, the method can include processing the intraoperative image data to generate a point cloud depth map of the scene. Then, the method can utilize a registration algorithm that maps the point cloud depth map to the preoperative medical scan data. In some embodiments, the processing device of the imaging system can generate a 3D mesh based on the point cloud depth map that can be used in, for example, generating the 3D virtual image of the scene. Accordingly, the registration algorithm can be initiated based on the point cloud depth map rather than the 3D mesh. In some aspects of the present technology, utilizing the point cloud depth map allows the registration to be run in parallel to the generation of the 3D mesh and subsequent synthesis of the 3D virtual image, thereby increasing the processing speed of the imaging system.

In some embodiments, the processing device of the imaging system can implement/utilize a registration algorithm that processes increasing numbers/densities of points in the point cloud depth map in a stepped manner until a sufficient registration accuracy is achieved. For example, the registration algorithm can initially process a first number of points in the point cloud and, after reaching a predefined accuracy, continue registration based on a greater second number of points in the point cloud. In some embodiments, the method can include processing increasing numbers of points in the point cloud (e.g., steps of increasing number) until the sufficient registration accuracy is reached. In some aspects of the present technology, such stepped processing can increase the processing speed of the imaging system.

In some embodiments, the processing device of the imaging system (and/or another processing device) can implement a method for evaluating the accuracy of a computed intraoperative registration transform that defines a mapping between the intraoperative image data and the preoperative image data. More specifically, the method can include (i) receiving historical registration data including historical registration transforms, (ii) defining spatial neighborhoods around the registration transforms, (iii) classifying/labeling the registration transforms (e.g., as "good" transforms or "bad" transforms), and (iv) training a machine learning model based on the spatial neighborhoods and classifications. The method can further include determining the accuracy of the intraoperative registration transform by defining a spatial neighborhood around the intraoperative registration transform and inputting the intraoperative registration transform into the machine learning model, which can output a fitness score (e.g., "good," "bad") for the registration. In some aspects of the present technology, evaluating the neighborhood of values of around a given registration transform—rather than the transform alone—increases the confidence in the evaluation of registration accuracy.

Specific details of several embodiments of the present technology are described herein with reference to FIGS. 1-12. The present technology, however, can be practiced without some of these specific details. In some instances, well-known structures and techniques often associated with camera arrays, light field cameras, image reconstruction, registration processes, and the like have not been shown in detail so as not to obscure the present technology. The terminology used in the description presented below is intended to be interpreted in its broadest reasonable manner, even though it is being used in conjunction with a detailed description of certain specific embodiments of the disclosure. Certain terms can even be emphasized below; however, any terminology intended to be interpreted in any restricted manner will be overtly and specifically defined as such in this Detailed Description section.

Moreover, although frequently described in the context of registering preoperative image data to intraoperative image data of a surgical scene, the registrations techniques of the present technology can be used to register image data of other types. For example, the systems and methods of the present technology can be used more generally to register any previously-captured data to corresponding real-time or near-real-time image data of a scene to generate a mediated reality view of the scene including a combination/fusion of the previously-captured data and the real-time images.

The accompanying figures depict embodiments of the present technology and are not intended to be limiting of its scope. The sizes of various depicted elements are not necessarily drawn to scale, and these various elements can be arbitrarily enlarged to improve legibility. Component details can be abstracted in the figures to exclude details such as position of components and certain precise connections between such components when such details are unnecessary for a complete understanding of how to make and use the present technology. Many of the details, dimensions, angles, and other features shown in the Figures are merely illustrative of particular embodiments of the disclosure. Accordingly, other embodiments can have other details, dimensions, angles, and features without departing from the spirit or scope of the present technology.

The headings provided herein are for convenience only and should not be construed as limiting the subject matter disclosed.

I. SELECTED EMBODIMENTS OF IMAGING SYSTEMS

FIG. 1 is a schematic view of an imaging system 100 ("system 100") in accordance with embodiments of the present technology. In some embodiments, the system 100 can be a synthetic augmented reality system, a mediated-reality imaging system, and/or a computational imaging system. In the illustrated embodiment, the system 100 includes a processing device 102 that is operably/communicatively coupled to one or more display devices 104, one or more input controllers 106, and a camera array 110. In other embodiments, the system 100 can comprise additional, fewer, or different components. In some embodiments, the system 100 can include some features that are generally similar or identical to those of the mediated-reality imaging systems disclosed in (i) U.S. patent application Ser. No. 16/586,375, titled "CAMERA ARRAY FOR A MEDIATED-REALITY SYSTEM," and filed Sep. 27, 2019 and/or (ii) U.S. patent application Ser. No. 15/930,305, titled "METHODS AND SYSTEMS FOR IMAGING A SCENE, SUCH AS A MEDICAL SCENE, AND TRACKING OBJECTS WITHIN THE SCENE," filed May 12, 2020, each of which is incorporated herein by reference in its entirety.

In the illustrated embodiment, the camera array 110 includes a plurality of cameras 112 (identified individually as cameras 112a-112n; which can also be referred to as first cameras) that are each configured to capture images of a scene 108 from a different perspective (e.g., first image data). The scene 108 can be a surgical scene including, for example, a patient undergoing surgery or another medical procedure. In other embodiments, the scene 108 can be another type of scene. The camera array 110 further includes a plurality of dedicated object trackers 113 (identified individually as trackers 113a-113n) configured to capture positional data of one more objects, such as a tool 101 (e.g., a surgical tool) having a tip 109, to track the movement and/or orientation of the objects through/in the scene 108. In some embodiments, the cameras 112 and the trackers 113 are positioned at fixed locations and orientations (e.g., poses) relative to one another. For example, the cameras 112 and the trackers 113 can be structurally secured by/to a mounting structure (e.g., a frame) at predefined fixed locations and orientations. In some embodiments, the cameras 112 can be positioned such that neighboring cameras 112 share overlapping views of the scene 108. Likewise, the trackers 113 can be positioned such that neighboring trackers 113 share overlapping views of the scene 108. Therefore, all or a subset of the cameras 112 and the trackers 113 can have different extrinsic parameters, such as position and orientation.

In some embodiments, the cameras 112 in the camera array 110 are synchronized to capture images of the scene 108 substantially simultaneously (e.g., within a threshold temporal error). In some embodiments, all or a subset of the cameras 112 can be light-field/plenoptic/RGB cameras that are configured to capture information about the light field emanating from the scene 108 (e.g., information about the intensity of light rays in the scene 108 and also information about a direction the light rays are traveling through space). Therefore, in some embodiments the images captured by the cameras 112 can encode depth information representing a surface geometry of the scene 108. In some embodiments, the cameras 112 are substantially identical. In other embodiments, the cameras 112 can include multiple cameras of different types. For example, different subsets of the cameras 112 can have different intrinsic parameters such as focal length, sensor type, optical components, and the like. The cameras 112 can have charge-coupled device (CCD) and/or complementary metal-oxide semiconductor (CMOS) image sensors and associated optics. Such optics can include a variety of configurations including lensed or bare individual image sensors in combination with larger macro lenses, micro-lens arrays, prisms, and/or negative lenses. For example, the cameras 112 can be separate light-field cameras each having their own image sensors and optics. In other embodiments, some or all of the cameras 112 can comprise separate microlenslets (e.g., lenslets, lenses, microlenses) of a microlens array (MLA) that share a common image sensor.

In some embodiments, the trackers 113 are imaging devices, such as infrared (IR) cameras that are each configured to capture images of the scene 108 from a different perspective compared to other ones of the trackers 113. Accordingly, the trackers 113 and the cameras 112 can have different spectral sensitives (e.g., infrared vs. visible wavelength). In some embodiments, the trackers 113 are configured to capture image data of a plurality of optical markers (e.g., fiducial markers, marker balls) in the scene 108, such as markers 111 coupled to the tool 101.

In the illustrated embodiment, the camera array 110 further includes a depth sensor 114. In some embodiments, the depth sensor 114 includes (i) one or more projectors 116 configured to project a structured light pattern onto/into the scene 108 and (ii) one or more depth cameras 118 (which can also be referred to as second cameras) configured to capture second image data of the scene 108 including the structured light projected onto the scene 108 by the projector 116. The projector 116 and the depth cameras 118 can operate in the same wavelength and, in some embodiments, can operate in a wavelength different than the cameras 112. For example, the cameras 112 can capture the first image data in the visible spectrum, while the depth cameras 118 capture the second image data in the infrared spectrum. In some embodiments, the depth cameras 118 have a resolution that is less than a resolution of the cameras 112. For example, the depth cameras 118 can have a resolution that is less than 70%, 60%, 50%, 40%, 30%, or 20% of the resolution of the cameras 112. In other embodiments, the depth sensor 114 can include other types of dedicated depth detection hardware (e.g., a LiDAR detector) for determining the surface geometry of the scene 108. In other embodiments, the camera array 110 can omit the projector 116 and/or the depth cameras 118.

In the illustrated embodiment, the processing device 102 includes an image processing device 103 (e.g., an image processor, an image processing module, an image processing unit), a registration processing device 105 (e.g., a registration processor, a registration processing module, a registration processing unit), and a tracking processing device 107 (e.g., a tracking processor, a tracking processing module, a tracking processing unit). The image processing device 103 is configured to (i) receive the first image data captured by the cameras 112 (e.g., light-field images, light field image data, RGB images) and depth information from the depth sensor 114 (e.g., the second image data captured by the depth cameras 118), and (ii) process the image data and depth information to synthesize (e.g., generate, reconstruct, render) a three-dimensional (3D) output image of the scene 108 corresponding to a virtual camera perspective. The output image can correspond to an approximation of an image of the scene 108 that would be captured by a camera placed at an arbitrary position and orientation corresponding to the virtual camera perspective. In some embodiments, the image processing device 103 is further configured to receive and/or store calibration data for the cameras 112 and/or the depth cameras 118 and to synthesize the output image based on the image data, the depth information, and/or the calibration data. More specifically, the depth information and calibration data can be used/combined with the images from the cameras 112 to synthesize the output image as a 3D (or stereoscopic 2D) rendering of the scene 108 as viewed from the virtual camera perspective. In some embodiments, the image processing device 103 can synthesize the output image using any of the methods disclosed in U.S. patent application Ser. No. 16/457,780, titled "SYNTHESIZING AN IMAGE FROM A VIRTUAL PERSPECTIVE USING PIXELS FROM A PHYSICAL IMAGER ARRAY WEIGHTED BASED ON DEPTH ERROR SENSITIVITY," which is incorporated herein by reference in its entirety. In other embodiments, the image processing device 103 is configured to generate the virtual camera perspective based only on the images captured by the cameras 112—without utilizing depth information from the depth sensor 114. For example, the image processing device 103 can generate the virtual camera perspective by interpolating between the different images captured by one or more of the cameras 112.

The image processing device 103 can synthesize the output image from images captured by a subset (e.g., two or more) of the cameras 112 in the camera array 110, and does not necessarily utilize images from all of the cameras 112. For example, for a given virtual camera perspective, the processing device 102 can select a stereoscopic pair of images from two of the cameras 112 that are positioned and oriented to most closely match the virtual camera perspective. In some embodiments, the image processing device 103 (and/or the depth sensor 114) is configured to estimate a depth for each surface point of the scene 108 relative to a common origin and to generate a point cloud and/or a 3D mesh that represents the surface geometry of the scene 108.

For example, in some embodiments the depth cameras 118 of the depth sensor 114 can detect the structured light projected onto the scene 108 by the projector 116 to estimate depth information of the scene 108. In some embodiments, the image processing device 103 can estimate depth from multiview image data from the cameras 112 using techniques such as light field correspondence, stereo block matching, photometric symmetry, correspondence, defocus, block matching, texture-assisted block matching, structured light, and the like, with or without utilizing information collected by the depth sensor 114. In other embodiments, depth may be acquired by a specialized set of the cameras 112 performing the aforementioned methods in another wavelength.

In some embodiments, the registration processing device 105 is configured to receive and/or store previously-captured image data, such as preoperative image data of a three-dimensional volume of a patient. The preoperative image data can include, for example, computerized tomography (CT) scan data, magnetic resonance imaging (MRI) scan data, ultrasound images, fluoroscope images, and the like. As described in further detail below with reference to FIGS. 3-12, the registration processing device 105 is further configured to register the preoperative image data to the real-time images captured by the cameras 112 and/or the depth sensor 114 by, for example, determining one or more transforms/transformations/mappings between the two. The processing device 102 (e.g., the image processing device 103) can then apply the one or more transforms to the preoperative image data such that the preoperative image data can be aligned with (e.g., overlaid on) the output image of the scene 108 in real-time or near real time on a frame-by-frame basis, even as the virtual perspective changes. That is, the image processing device 103 can fuse the preoperative image data with the real-time output image of the scene 108 to present a mediated-reality view that enables, for example, a surgeon to simultaneously view a surgical site in the scene 108 and the underlying 3D anatomy of a patient undergoing an operation.

In some embodiments, the tracking processing device 107 can process positional data captured by the trackers 113 to track objects (e.g., the tool 101) within the vicinity of the scene 108. For example, the tracking processing device 107 can determine the position of the markers 111 in the 2D images captured by two or more of the trackers 113, and can compute the 3D position of the markers 111 via triangulation of the 2D positional data. More specifically, in some embodiments the trackers 113 include dedicated processing hardware for determining positional data from captured images, such as a centroid of the markers 111 in the captured images. The trackers 113 can then transmit the positional data to the tracking processing device 107 for determining the 3D position of the markers 111. In other embodiments, the tracking processing device 107 can receive the raw image data from the trackers 113. In a surgical application, for example, the tracked object may comprise a surgical instrument, a hand or arm of a physician or assistant, and/or another object having the markers 111 mounted thereto. In some embodiments, the processing device 102 can recognize the tracked object as being separate from the scene 108, and can apply a visual effect to the 3D output image to distinguish the tracked object by, for example, highlighting the object, labeling the object, and/or applying a transparency to the object.

In some embodiments, functions attributed to the processing device 102, the image processing device 103, the registration processing device 105, and/or the tracking processing device 107 can be practically implemented by two or more physical devices. For example, in some embodiments a synchronization controller (not shown) controls images displayed by the projector 116 and sends synchronization signals to the cameras 112 to ensure synchronization between the cameras 112 and the projector 116 to enable fast, multi-frame, multi-camera structured light scans. Additionally, such a synchronization controller can operate as a parameter server that stores hardware specific configurations such as parameters of the structured light scan, camera settings, and camera calibration data specific to the camera configuration of the camera array 110. The synchronization controller can be implemented in a separate physical device from a display controller that controls the display device 104, or the devices can be integrated together.

The processing device 102 can comprise a processor and a non-transitory computer-readable storage medium that stores instructions that when executed by the processor, carry out the functions attributed to the processing device 102 as described herein. Although not required, aspects and embodiments of the present technology can be described in the general context of computer-executable instructions, such as routines executed by a general-purpose computer, e.g., a server or personal computer. Those skilled in the relevant art will appreciate that the present technology can be practiced with other computer system configurations, including Internet appliances, hand-held devices, wearable computers, cellular or mobile phones, multi-processor systems, microprocessor-based or programmable consumer electronics, set-top boxes, network PCs, mini-computers, mainframe computers and the like. The present technology can be embodied in a special purpose computer or data processor that is specifically programmed, configured or constructed to perform one or more of the computer-executable instructions explained in detail below. Indeed, the term "computer" (and like terms), as used generally herein, refers to any of the above devices, as well as any data processor or any device capable of communicating with a network, including consumer electronic goods such as game devices, cameras, or other electronic devices having a processor and other components, e.g., network communication circuitry.

The present technology can also be practiced in distributed computing environments, where tasks or modules are performed by remote processing devices, which are linked through a communications network, such as a Local Area Network ("LAN"), Wide Area Network ("WAN"), or the Internet. In a distributed computing environment, program modules or sub-routines can be located in both local and remote memory storage devices. Aspects of the present technology described below can be stored or distributed on computer-readable media, including magnetic and optically readable and removable computer discs, stored as in chips (e.g., EEPROM or flash memory chips). Alternatively, aspects of the present technology can be distributed electronically over the Internet or over other networks (including wireless networks). Those skilled in the relevant art will recognize that portions of the present technology can reside on a server computer, while corresponding portions reside on a client computer. Data structures and transmission of data particular to aspects of the present technology are also encompassed within the scope of the present technology.

The virtual camera perspective can be controlled by an input controller 106 that provides a control input corresponding to the location and orientation of the virtual camera perspective. The output images corresponding to the virtual camera perspective can be outputted to the display device 104. In some embodiments, the image processing device 103 can vary the perspective, the depth of field (e.g., aperture), the focus plane, and/or another parameter of the virtual camera (e.g., based on an input from the input controller) to generate different 3D output images without physically moving the camera array 110. The display device 104 is configured to receive output images (e.g., the synthesized 3D rendering of the scene 108) and to display the output images for viewing by one or more viewers. In some embodiments, the processing device 102 can receive and process inputs from the input controller 106 and process the captured images from the camera array 110 to generate output images corresponding to the virtual perspective in substantially real-time as perceived by a viewer of the display device 104 (e.g., at least as fast as the frame rate of the camera array 110). Additionally, the display device 104 can display a graphical representation on/in the image of the virtual perspective of any (i) tracked objects within the scene 108 (e.g., a surgical tool) and/or (ii) registered or unregistered preoperative image data.

The display device 104 can comprise, for example, a head-mounted display device, a monitor, a computer display, and/or another display device. In some embodiments, the input controller 106 and the display device 104 are integrated into a head-mounted display device and the input controller 106 comprises a motion sensor that detects position and orientation of the head-mounted display device. The virtual camera perspective can then be derived to correspond to the position and orientation of the head-mounted display device 104 in the same reference frame and at the calculated depth (e.g., as calculated by the depth sensor 114) such that the virtual perspective corresponds to a perspective that would be seen by a viewer wearing the head-mounted display device 104. Thus, in such embodiments the head-mounted display device 104 can provide a real-time rendering of the scene 108 as it would be seen by an observer without the head-mounted display device 104. Alternatively, the input controller 106 can comprise a user-controlled control device (e.g., a mouse, pointing device, handheld controller, gesture recognition controller, etc.) that enables a viewer to manually control the virtual perspective displayed by the display device 104.

Figure 2:
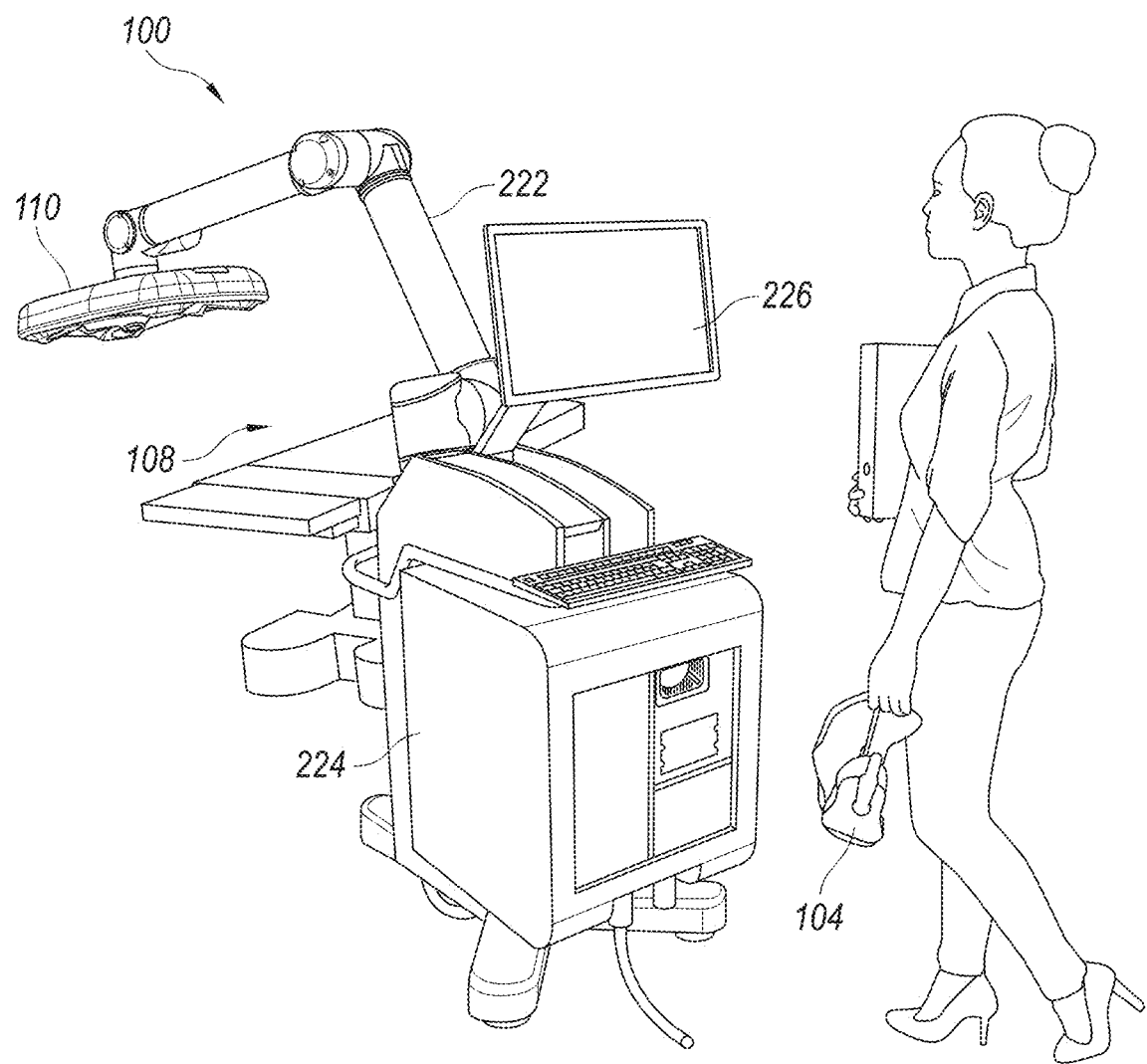
FIG. 2 is a perspective view of a surgical environment employing the imaging system of FIG. 1 for a surgical application in accordance with embodiments of the present technology.

FIG. 2 is a perspective view of a surgical environment employing the system 100 for a surgical application in accordance with embodiments of the present technology. In the illustrated embodiment, the camera array 110 is positioned over the scene 108 (e.g., a surgical site) and supported/positioned via a movable arm 222 that is operably coupled to a workstation 224. In some embodiments, the arm 222 can be manually moved to position the camera array 110 while, in other embodiments, the arm 222 can be robotically controlled in response to the input controller 106 (FIG. 1) and/or another controller. In the illustrated embodiment, the display device 104 is a head-mounted display device (e.g., a virtual reality headset, augmented reality headset, etc.). The workstation 224 can include a computer to control various functions of the processing device 102, the display device 104, the input controller 106, the camera array 110, and/or other components of the system 100 shown in FIG. 1. Accordingly, in some embodiments the processing device 102 and the input controller 106 are each integrated in the workstation 224. In some embodiments, the workstation 224 includes a secondary display 226 that can display a user interface for performing various configuration functions, a mirrored image of the display on the display device 104, and/or other useful visual images/indications.

II. SELECTED EMBODIMENTS OF REGISTRATION TECHNIQUES

Figure 3:
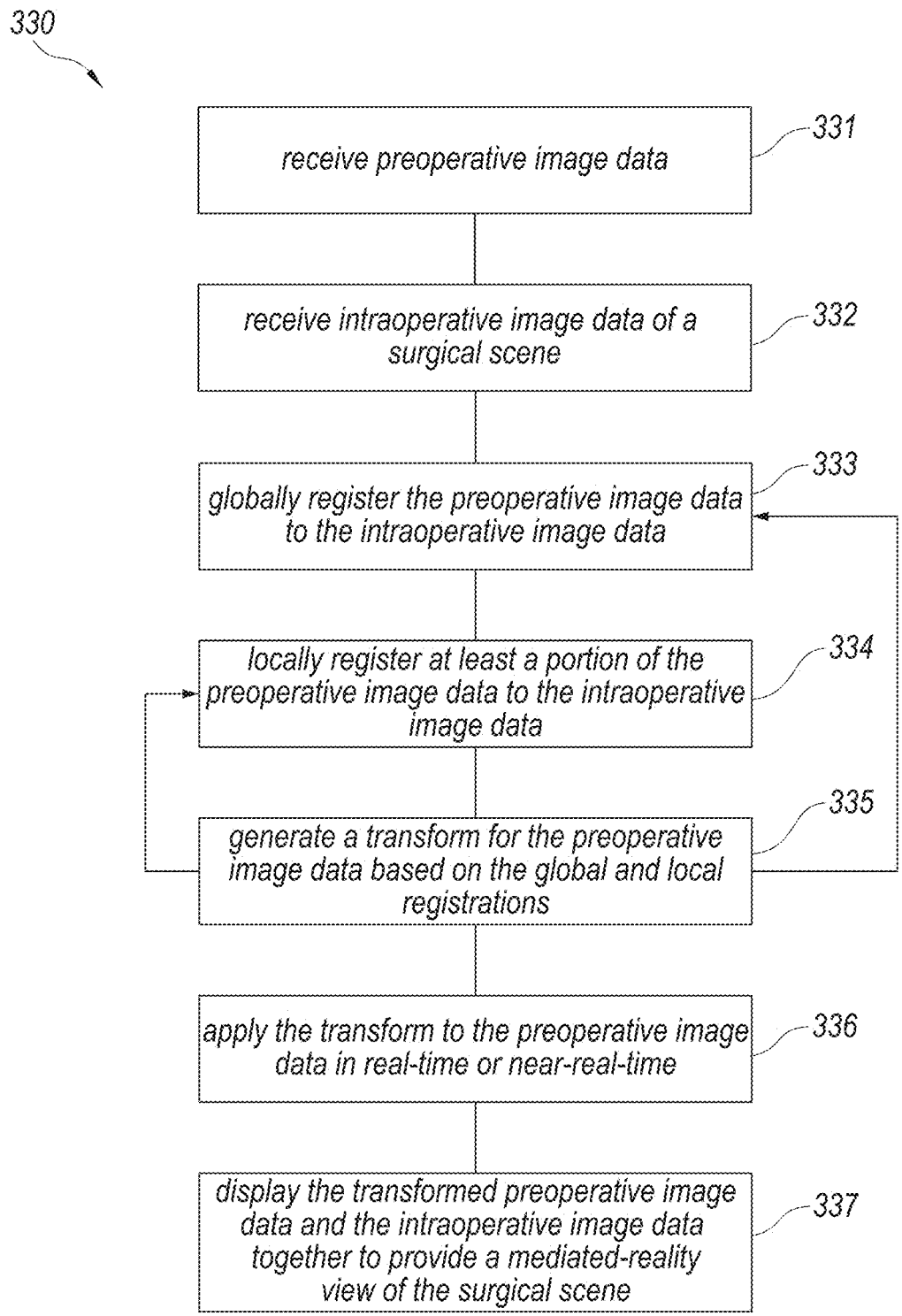
FIG. 3 is a flow diagram of a process or method for registering preoperative image data to intraoperative image data to generate a mediated reality view of a surgical scene in accordance with embodiments of the present technology.
Figure 4A:
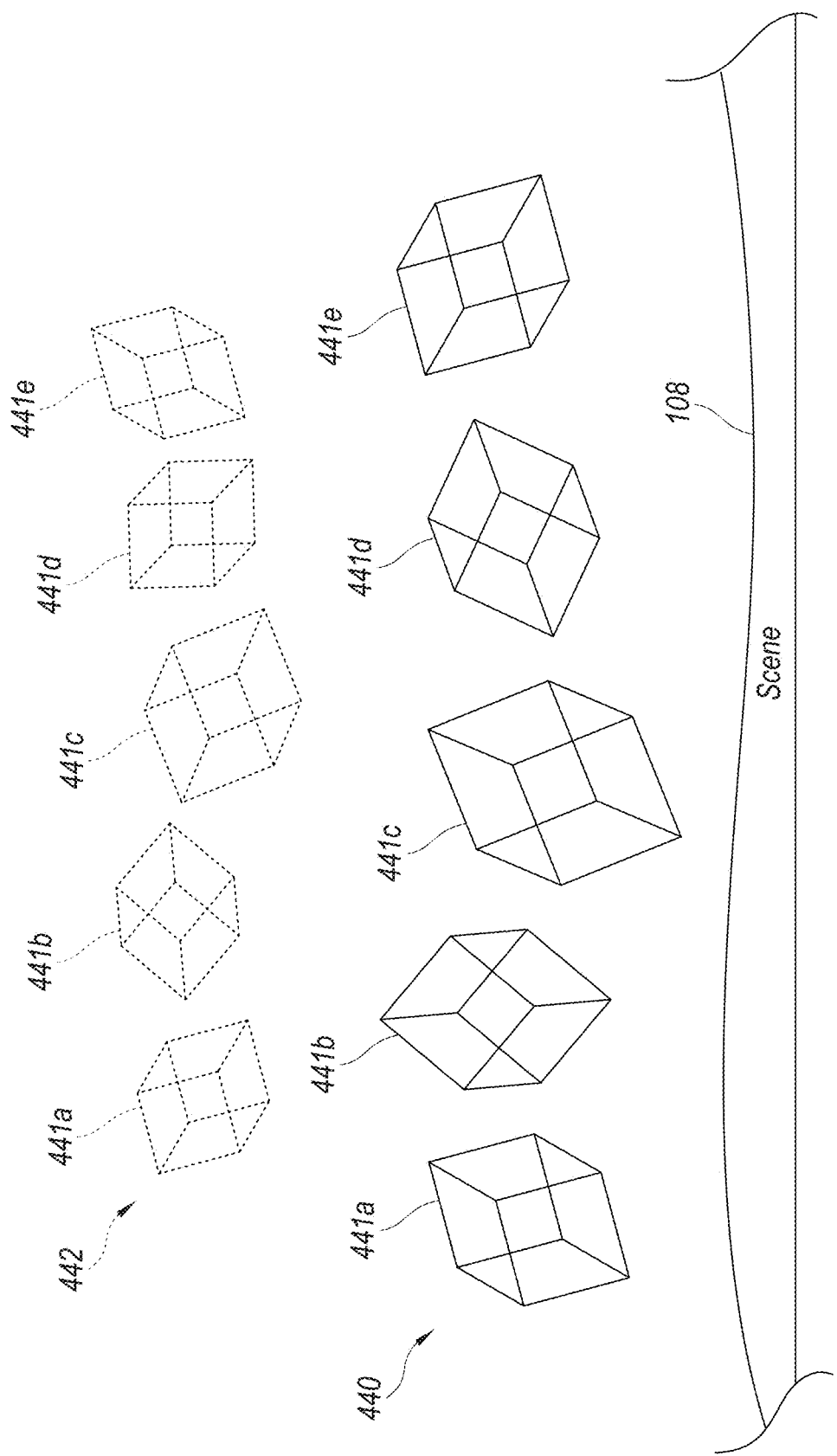
Figure 4C:
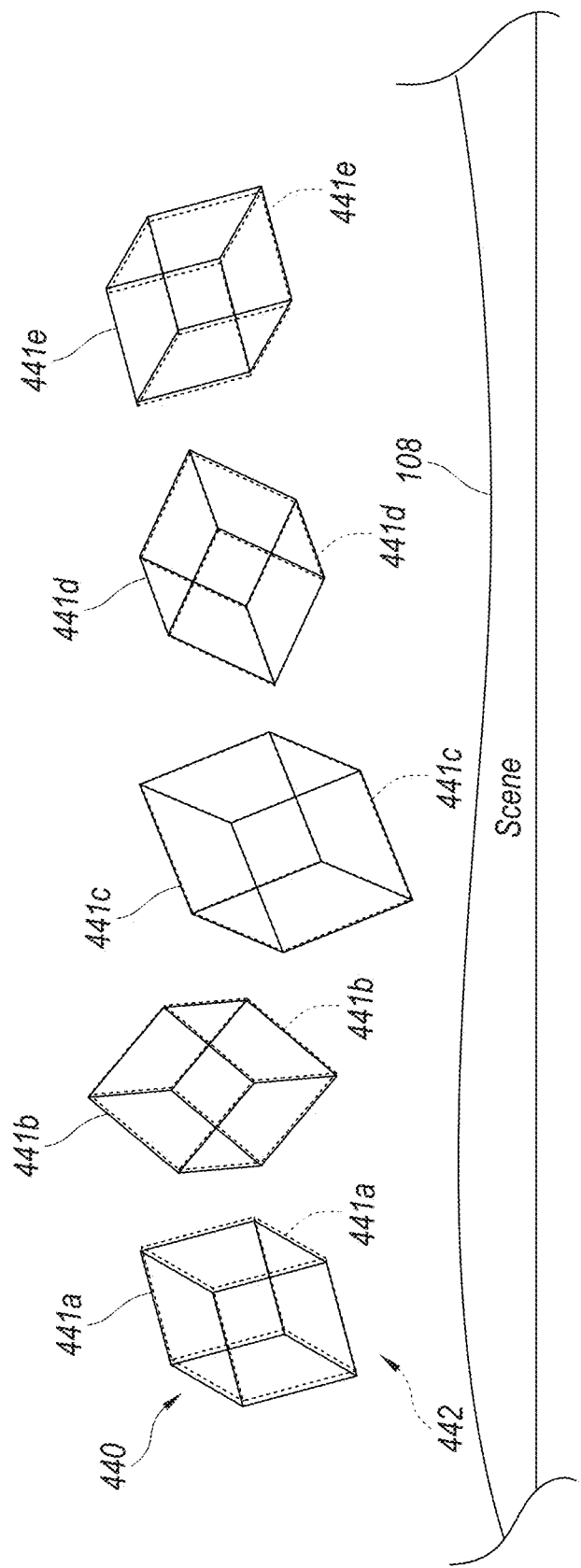

FIG. 3 is a flow diagram of a process or method 330 for registering preoperative image data to/with intraoperative image data to generate a mediated reality view of a surgical scene in accordance with embodiments of the present technology. Although some features of the method 330 are described in the context of the system 100 shown in FIGS. 1 and 2 for the sake of illustration, one skilled in the art will readily understand that the method 330 can be carried out using other suitable systems and/or devices described herein. Similarly, while reference is made herein to preoperative image data, intraoperative image data, and a surgical scene, the method 330 can be used to register and display other types of information about other scenes. For example, the method 330 can be used more generally to register any previously-captured image data to corresponding real-time or near-real-time image data of a scene to generate a mediated reality view of the scene including a combination/fusion of the previously-captured image data and the real-time images. FIGS. 4A-4C are schematic illustrations of intraoperative image data 440 of an object within the field of view of the camera array 110 and corresponding preoperative image data 442 of the object illustrating various stages of the method 330 of FIG. 3 in accordance with embodiments of the present technology. Accordingly, some aspects of the method 330 are described in the context of FIGS. 4A-4C.

At block 331, the method 330 includes receiving preoperative image data. As described in detail above, the preoperative image data can be, for example, medical scan data representing a three-dimensional volume of a patient, such as computerized tomography (CT) scan data, magnetic resonance imaging (MRI) scan data, ultrasound images, fluoroscope images, and the like. In some embodiments, the preoperative image data can comprise a point cloud or three-dimensional (3D) mesh.

At block 332, the method 330 includes receiving intraoperative image data of the surgical scene 108 from, for example, the camera array 110. The intraoperative image data can include real-time or near-real-time images of a patient in the scene 108 captured by the cameras 112 and/or the depth cameras 118. In some embodiments, the intraoperative image data includes (i) light-field images from the cameras 112 and (ii) images from the depth cameras 118 that include encoded depth information about the scene 108. In some embodiments, the preoperative image data corresponds to at least some features in the intraoperative image data. For example, the scene 108 can include a patient undergoing spinal surgery with their spine at least partially exposed. The preoperative image data can include CT scan data of the patient's spine taken before surgery and that comprises a complete 3D data set of at least a portion of the spine. Accordingly, various vertebrae or other features in the preoperative image data can correspond to portions of the patient's spine represented in the image data from the cameras 112, 118. In other embodiments, the scene 108 can include a patient undergoing another type of surgery, such as knee surgery, skull-based surgery, and so on, and the preoperative image data can include CT or other scan data of ligaments, bones, flesh, and/or other anatomy relevant to the particular surgical procedure.

More specifically, referring to FIG. 4A, the object can include a plurality of sub-portions 441 (identified individually as first through fifth sub-portions 441a-441e, respectively) represented in both the intraoperative image data 440 and the preoperative image data 442. The object can be, for example, a spine of a patient and the sub-portions 441 can comprise individual vertebrae of the spine. The preoperative image data 442 and the intraoperative image data 440 of the object typically exist in different coordinate systems such that the same features in both data sets (e.g., the sub-portions 441) are represented differently. In the illustrated embodiment, for example, each of the sub-portions 441 in the preoperative image data 442 is rotated, scaled, and/or translated relative to the corresponding one of the sub-portions 441 in the intraoperative image data 440 of the object.

Accordingly, at block 333, the method 330 includes globally registering the preoperative image data to the intraoperative image data to, for example, establish a transform/mapping/transformation between the intraoperative image data and the preoperative image data so that these data sets can be represented in the same coordinate system and subsequently displayed together. FIG. 4B, for example, shows the intraoperative image data 440 and the preoperative image data 442 of the object after global registration. In the illustrated embodiment, after globally registering the preoperative image data 442 to the intraoperative image data 440 of the object, the sub-portions 441 can be at least roughly aligned in each data set (e.g., in the intraoperative image space, coordinate system, and/or frame). In some embodiments, the global registration process matches (i) 3D points in a point cloud or a 3D mesh representing the preoperative image data to (ii) 3D points in a point cloud or a 3D mesh representing the intraoperative image data. In some embodiments, the system 100 (e.g., the registration processing device 105) can generate a 3D point cloud from the intraoperative image data from the depth cameras 118 of the depth sensor 114, and can register the point cloud to the preoperative image data by detecting positions of fiducial markers and/or feature points visible in both data sets. For example, where the preoperative image data comprises CT scan data, rigid bodies of bone surface calculated from the CT scan data can be registered to the corresponding points/surfaces of the point cloud. In other embodiments, the system 100 can employ other registration processes based on other methods of shape correspondence, and/or registration processes that do not rely on fiducial markers (e.g., markerless registration processes). In some embodiments, the registration/alignment process can include features that are generally similar or identical to the registration/alignment processes disclosed in U.S. Provisional patent application Ser. No. 16/749,963, titled "ALIGNING PREOPERATIVE SCAN IMAGES TO REAL-TIME OPERATIVE IMAGES FOR A MEDIATED-REALITY VIEW OF A SURGICAL SITE," filed Jan. 22, 2020, which is incorporated herein by reference in its entirety. In yet other embodiments, the global registration can be carried out using any of the registration methods described in detail below with reference to, for example, FIGS. 5-6E.

In some aspects of the present technology, an algorithm used to globally register the preoperative image data to the intraoperative image data does not require an alignment for initialization. That is, the global registration algorithm can generate a transform between the preoperative image data and the intraoperative image data even when no initial mapping is known. In some embodiments, referring again to FIG. 4B, the global registration process can result in a relatively loose alignment in which, for example, some of the sub-portions 441 are rotated, translated, and/or scaled differently from one another in the common coordinate space. Accordingly, at block 334 the method 330 can include locally registering at least a portion of the preoperative image data to the intraoperative image data. FIG. 4C, for example, shows the intraoperative image data 440 and the preoperative image data 442 of the object after local registration. In the illustrated embodiment, each of the sub-portions 441 has been locally registered to provide a tighter alignment than the global registration shown in FIG. 4B. In other embodiments, fewer than all the sub-portions 441 and/or different subsets of the sub-portions 441 can be locally registered. For example, only a vertebrae or vertebrae to be operated on can be locally registered while other ones of the vertebrae remain only globally registered or not registered at all. In some embodiments, the registration processing device 105 can utilize a local registration algorithm that requires a rough alignment for initialization, such as the result of the global registration (block 333). For example, the registration processing device 105 can utilize any feature or surface matching registration method to achieve a tight registration, such as iterative closest point (ICP), Coherent Point Drift (CPD), or algorithms based on probability density estimation like Gaussian Mixture Models (GMM).

At block 335, the method 330 can include generating one or more transforms for the preoperative image data based on the global and local registrations (blocks 333 and 334). The one or more transforms can be functions that define a mapping between the coordinate system of the preoperative image data and the coordinate system of the intraoperative image data. At block 336, the registration processing device 105 can include applying the transform to the preoperative image data in real-time or near-real-time. Applying the transform to the preoperative image data can substantially align the preoperative image data with the real-time or near-real-time images of the scene 108 captured with the camera array 110.

Finally, at block 337, the method 330 can include displaying the transformed preoperative image data and the intraoperative image data together to provide a mediated-reality view of the surgical scene. The view can be provided on the display device 104 to a viewer, such as a surgeon. More specifically, the processing device 102 can overlay the aligned preoperative image data on the output image of the scene 108 in real-time or near real time on a frame-by-frame basis, even as the virtual perspective changes. That is, the image processing device 103 can overlay the preoperative image data with the real-time output image of the scene 108 to present a mediated-reality view that enables, for example, a surgeon to simultaneously view a surgical site in the scene 108 and the underlying 3D anatomy of a patient undergoing an operation.

Referring to FIGS. 3-4C together, in some embodiments the position and/or shape of the object within the scene 108 may change over time. For example, the relative positions and orientations of the sub-portions 441, such as vertebrae, may change during a surgical procedure as the patient is operated on. Accordingly, the method 330 can include periodically reregistering the preoperative image data to the intraoperative image data globally (block 333) and/or locally (block 334). In some embodiments, reregistration can be triggered when an accuracy (e.g., score, level) of the registration falls below a threshold level. In some embodiments, for example, such accuracy determinations can be carried out using the methods for assessing registration accuracy described in detail below with reference to FIG. 12.

Figure 5:
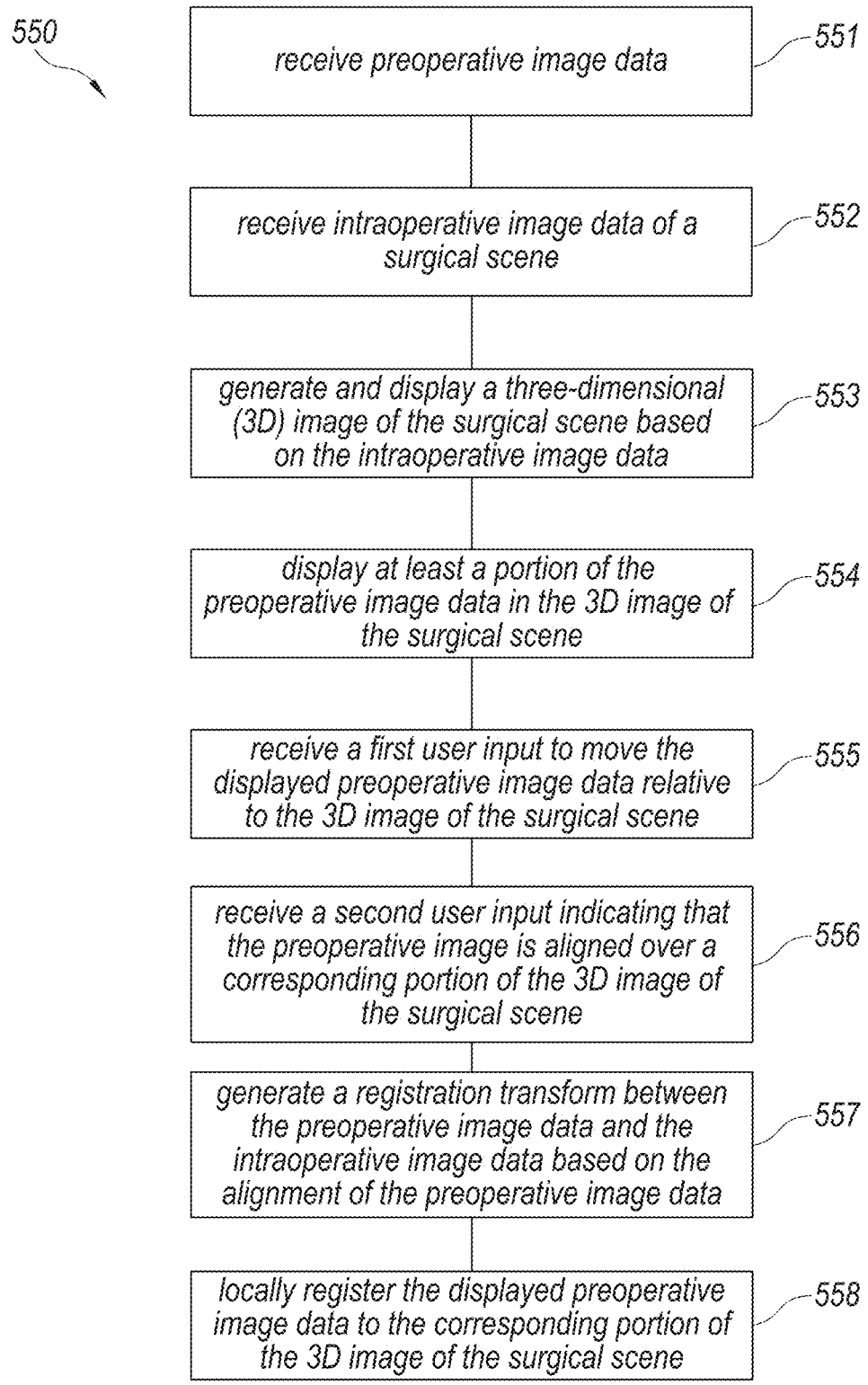
FIG. 5 is a flow diagram of a process or method for registering preoperative image data to intraoperative image data in accordance with embodiments of the present technology.

FIG. 5 is a flow diagram of a process or method 550 for registering preoperative image data to intraoperative image data in accordance with embodiments of the present technology. In some embodiments, the method 550 can be used to globally register the preoperative image data to the intraoperative image data at block 333 of the method 330 described in detail above with reference to FIGS. 3-4C. Although some features of the method 550 are described in the context of the system 100 shown in FIGS. 1 and 2 for the sake of illustration, one skilled in the art will readily understand that the method 550 can be carried out using other suitable systems and/or devices described herein. FIGS. 6A-6E are perspective views of output images of the scene 108 (e.g., a surgical scene) generated by the system 100 and viewable to a viewer, and illustrating various stages of the method 550 of FIG. 5 in accordance with embodiments of the present technology. Accordingly, some aspects of the method 550 are described in the context of FIGS. 6A-6E.

At block 551, the method 550 includes receiving preoperative image data. As described in detail above, the preoperative image data can comprise medical scan data representing a three-dimensional volume of a patient, such as computerized tomography CT scan data. At block 552, the method 550 includes receiving intraoperative image data of the surgical scene 108 from the camera array 110. As described in detail above, the intraoperative image data can include real-time or near-real-time images from the cameras 112 and/or the depth cameras 118, such as images of a patient's spine undergoing spinal surgery.

Figure 6A:
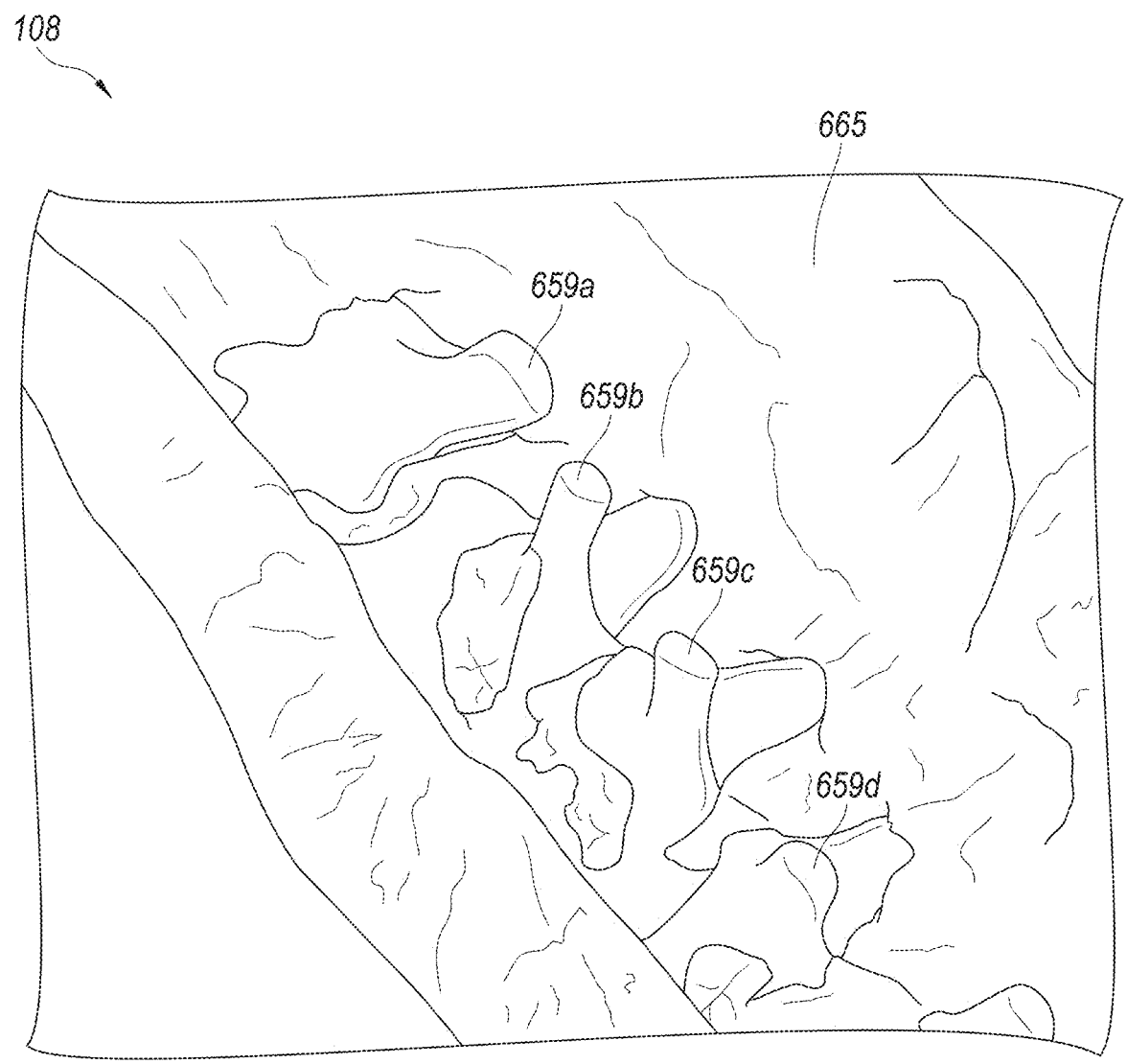
FIGS. 6A-6E are perspective views of output images of a surgical scene generated by the imaging system of FIG. 1, and illustrating various stages of the method of FIG. 5 in accordance with embodiments of the present technology.

At block 553, the method 550 includes generating and displaying a 3D output image/view of the surgical scene based on the intraoperative image data. As described in detail above with reference to FIG. 1, the processing device 102 can receive intraoperative image data from the depth sensor 114 and the cameras 112 and process the intraoperative image data to synthesize (e.g., generate, reconstruct, render) the three-3D output image of the scene 108 corresponding to a virtual camera perspective selected by, for example, the input controller 106. The 3D output image can correspond to an approximation of an image of the scene 108 that would be captured by a camera placed at an arbitrary position and orientation corresponding to the virtual camera perspective, and can be updated and displayed to a user via the display device 104 in substantially real-time as perceived by the user. FIG. 6A, for example, illustrates a 3D output image of the scene 108 viewable to the user (e.g., a surgeon) viewing the display device 104. In some embodiments, the scene 108 can include an object of interest (e.g., for registration purposes). In the illustrated embodiment, for example, the scene 108 is a spinal surgical scene including vertebrae 659 (identified individually as first through fourth vertebrae 659a-659d, respectively) exposed from flesh 665 of a patient during, for example, a spinal fusion or other spinal surgical procedure.

Figure 6B:
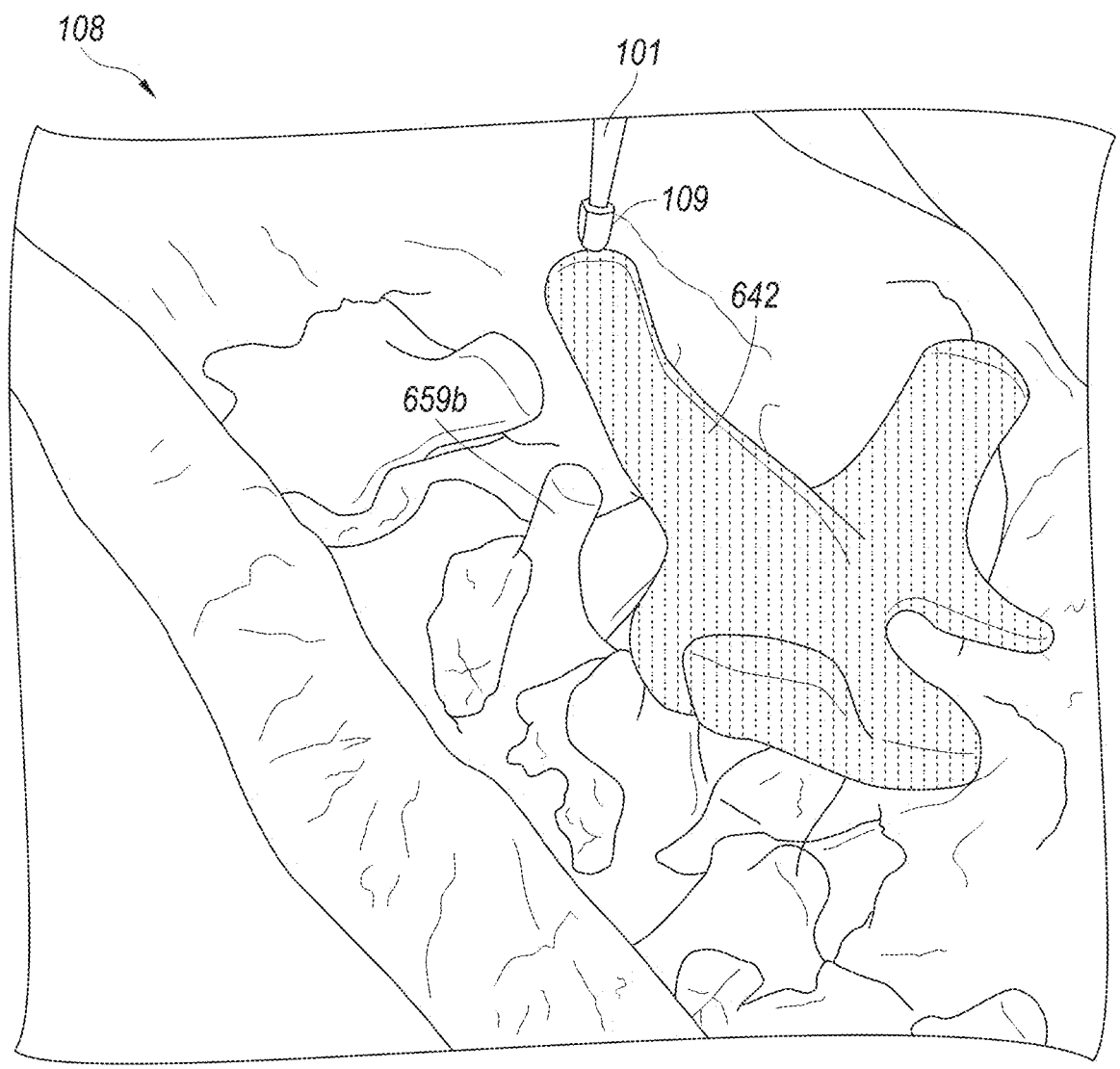

At block 554, the method 550 includes displaying at least a portion of the preoperative image data in the 3D output image of the surgical scene. The preoperative image data can be of/correspond to the object of interest in the scene 108 and can be unregistered to the interoperative image data. In some embodiments, the preoperative image data can be overlaid over the 3D output image of the surgical scene such that it is simultaneously viewable by the user. FIG. 6B, for example, illustrates preoperative image data 642 overlaid over the output image of the scene 108. In the illustrated embodiment, the preoperative image data 642 includes CT scan data of the second vertebra 659b. In some embodiments, the displayed preoperative image data 642 can be a segmented portion of a CT scan including information about multiple ones of the vertebrae. That is, the preoperative image data 642 overlaid over the virtual rendering of the scene 108 can be a portion or segment of a larger set of preoperative image data. In some embodiments, the system 100 can display the preoperative image data 642 based on the position of the tool 101 within the scene. In the illustrated embodiment, for example, the preoperative image data 642 is displayed at the tip 109 of the tool 101 and is thus movable through the scene 108. In some embodiments, the system 100 can render all or a portion of the tool 101 in the scene 108 (e.g., as shown in FIG. 6B) while, in other embodiments, the tool 101 can be omitted from the 3D output image.

Figure 6C:
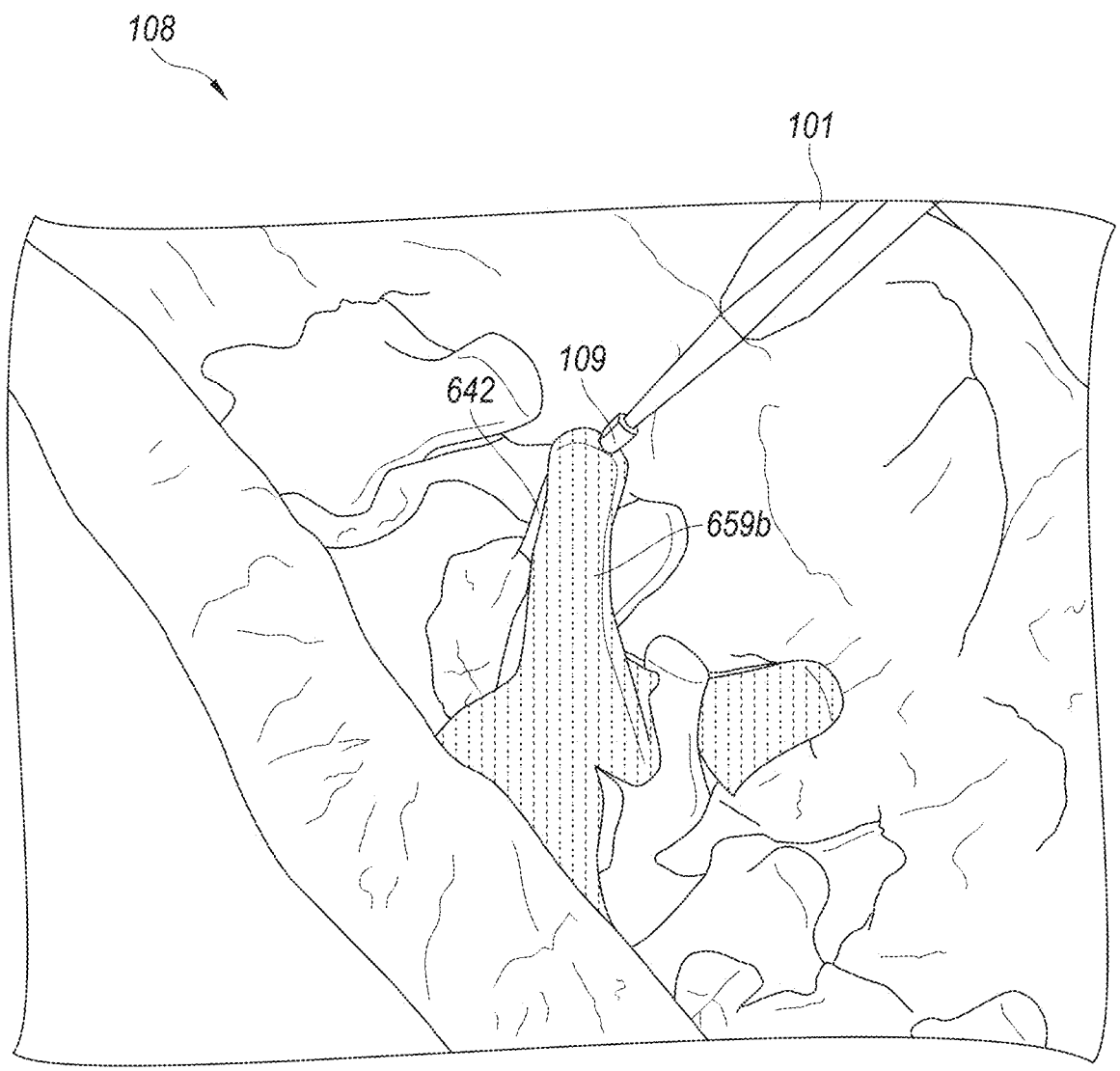
Figure 6D:
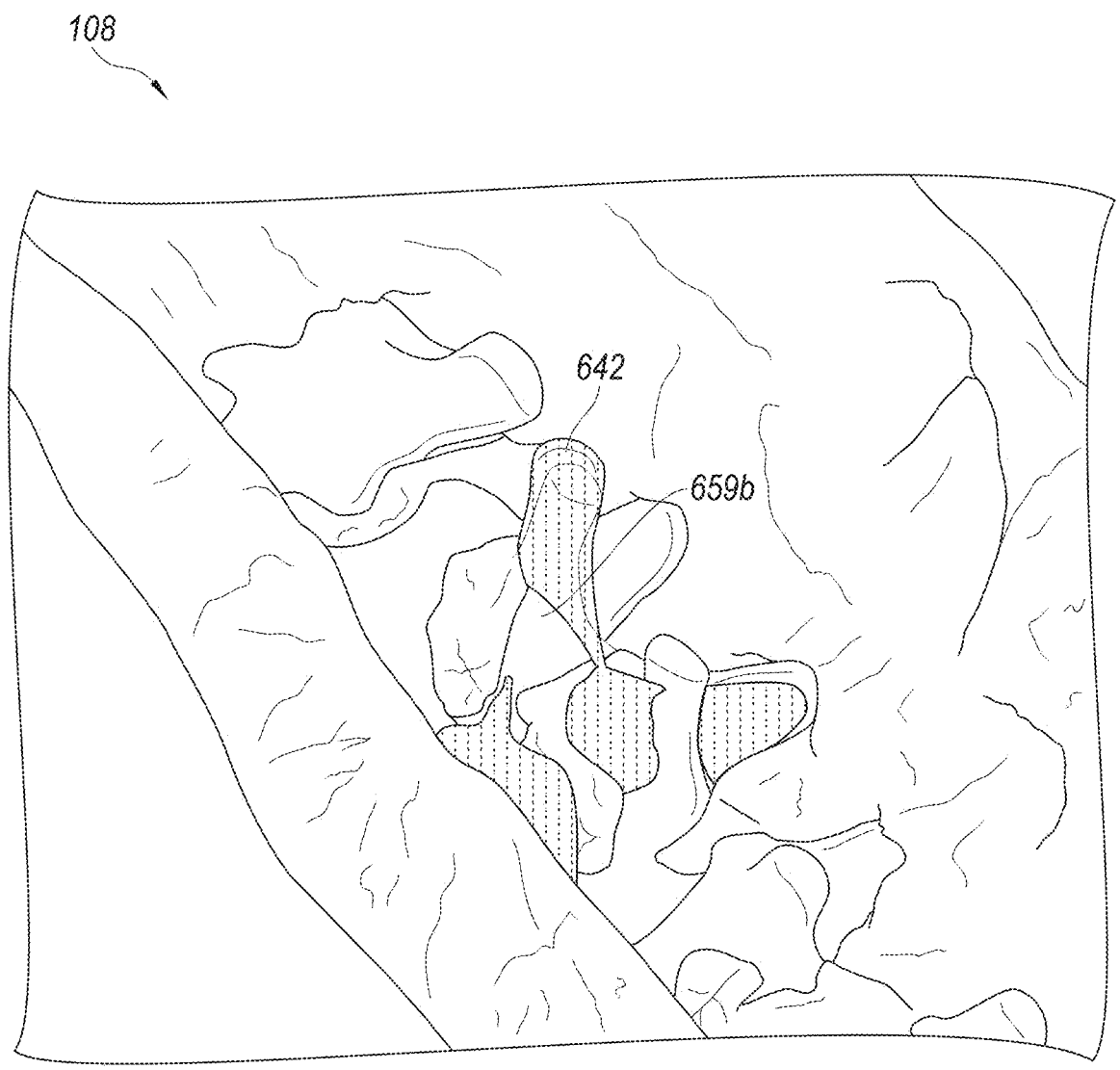

At block 555, the method 550 includes receiving a first user input to move the displayed preoperative image data relative to the 3D output image of the surgical scene. The first user input can be to manually align the displayed preoperative image data over a corresponding portion of the 3D output image of the surgical scene. Referring to FIGS. 6C and 6D together, for example, the user can move the tool 101 to translate (e.g., drag), rotate, and/or otherwise move the preoperative image data 642 relative to (e.g., over) the rendering of the scene 108 until it is generally aligned with the corresponding second vertebra 659b. That is, the user can physically manipulate the tool 101 relative to the surgical scene 108 to generally align/register the preoperative image data 642 with the intraoperative image data (e.g., the second vertebra 659b). In some embodiments, the system 100 can track the movement of the tool 101 relative to the scene 108 via the trackers 113 and translate that movement into virtual movement of the preoperative image data 642. In other embodiments, the system 100 can track other objects in the scene 108, such as the user's hands (e.g., one or more of the user's fingers), and translate that movement into movement of the preoperative image data 642.

At block 556, the method 550 includes receiving a second user input indicating that the displayed preoperative image data is aligned over the corresponding portion of the 3D output image of the surgical scene. Referring to FIG. 6D, for example, the user can provide an indication to the system 100 to decouple the tool 101 (FIG. 6C) from the preoperative image data 642 after the user has generally aligned the preoperative image data 642 with the intraoperative image data of the second vertebra 659b. In some embodiments, the second user input can include a button press (e.g., of a button on the tool 101), a voice command, a hand motion, and/or another suitable indication recognizable by the system 100. That is, after dragging the preoperative image data 642 into position, the user can "drop" the preoperative image data at the position by providing an indication to the system 100. In other embodiments, the system 100 can automatically detect that the preoperative image data is aligned over the corresponding portion of the 3D output image.

At block 557, the method 550 can include generating a registration transform between the preoperative image data and the intraoperative image data based on the alignment of the preoperative image data with the corresponding portion of the 3D output image. As described in detail above with reference to FIGS. 3-4C, for example, the registration transform can be a global transform that defines a mapping between the coordinate system of the preoperative image data and the coordinate system of the intraoperative image data.

Figure 6E:
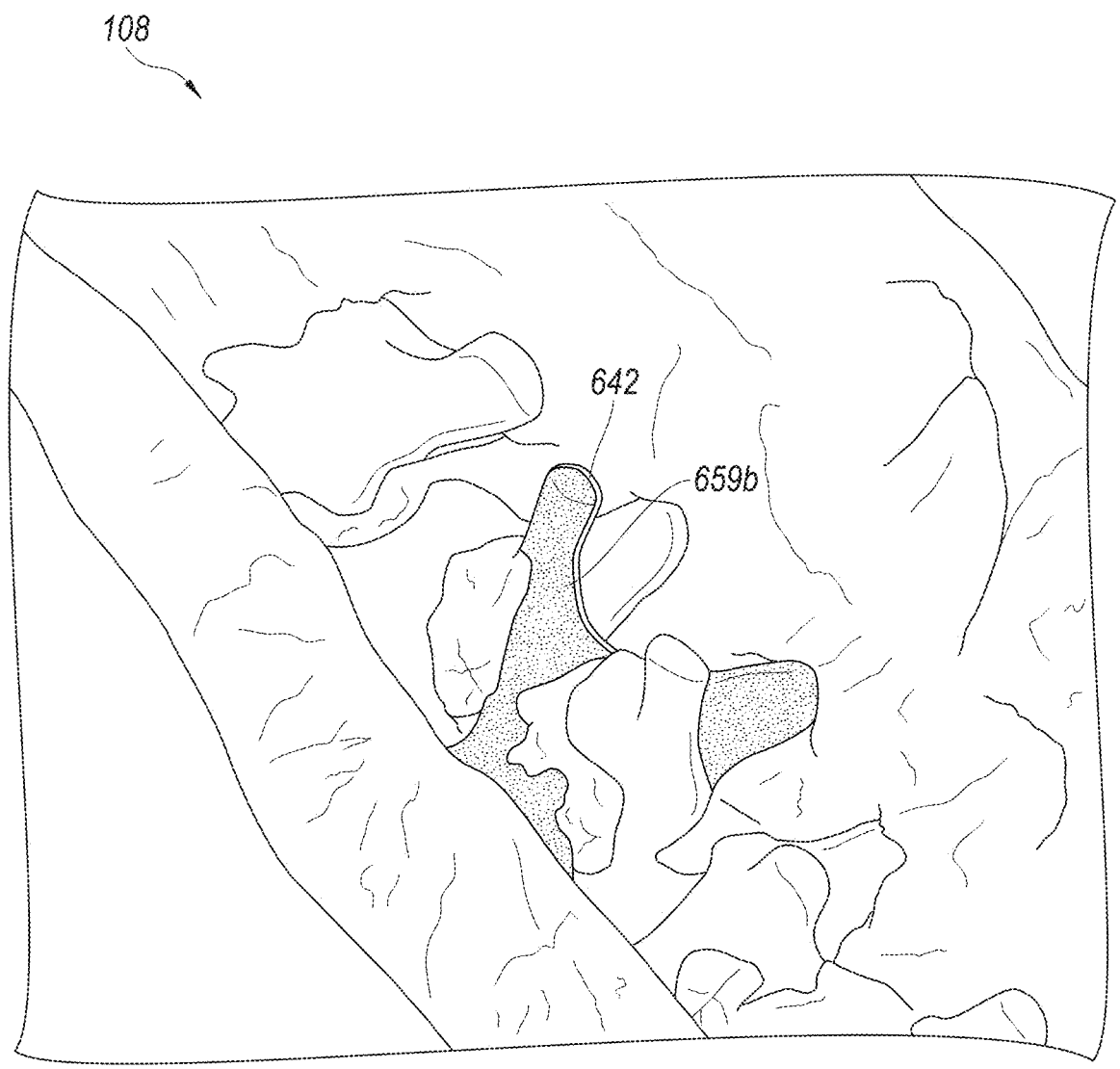

At block 558, the method 550 can include locally registering the displayed preoperative image data to the corresponding portion of the 3D output image of the surgical scene. As described in detail above with reference to FIGS. 3-4C, and as shown in FIG. 6E, the local registration can tighten/improve the alignment of the preoperative image data 642 to the intraoperative image data (e.g., the second vertebra 659b) using, for example, an ICP algorithm, a CPD algorithm, a GMM algorithm, and/or another algorithm initialized with the general alignment/transform provided by the user's manual registration of the preoperative image data 642 (blocks 555-557). In some embodiments, the local registration can "snap" the preoperative image data 642 into alignment. In some embodiments, the system 100 can prompt the user to repeat the manual alignment (blocks 555 and 556) if an accuracy of the local registration is not within a threshold tolerance.

In some aspects of the present technology, the method 550 allows a user to visualize a surgical scene, and to drag (block 555) and drop (block 556) preoperative image data into alignment with a corresponding portion of the scene before automatically snapping (block 558) the preoperative image data into further alignment. Moreover, the registration is based on the many points comprising the preoperative image data and the corresponding portion of the scene, and can be simple and easy for the user to carry out. In contrast, conventional registration techniques typically require a user (e.g., a surgeon) to repeatedly tap corresponding points in a CT scan and on a patient to register the CT scan to the patient. Accordingly, the registration is based on the relatively few points tapped and is time consuming for the user. For example, the user must repeatedly move their head to tap points on the CT scan and patient while, in contrast, the method 550 of the present technology provides an integrated registration that is simple and intuitive.

In some embodiments, the system 100 can attempt to locally register the preoperative image data to the scene 108 (block 557) while the user is attempting to manually align the preoperative image data (blocks 555 and 556). Based on the simultaneous local registration, the system 100 can help guide the user to manually place the preoperative image data at the correct position. For example, as the user moves the preoperative image data near to the correct position, the local registration algorithm can indicate that the preoperative image data is nearly aligned and provide an indication to the user. For example, referring to FIGS. 6A-6E, the system 100 can create a "gravity well" effect around the second vertebra 659b that draws/weights the preoperative image data 642 toward the second vertebra 659b from the view of the user. Alternatively or additionally, if the user manually moves the preoperative image data 642 close enough that local registration is successful, the system 100 can simply "snap" the preoperative image data 642 into alignment with the second vertebra 659b while the user is still guiding the preoperative image data 642 into position.

In some embodiments, after registering the portion of the preoperative image data displayed to the user (e.g., a segmented portion of a CT scan), the rest of the preoperative image data (e.g., the unsegmented or remaining portion of the CT scan) can be registered to the patient. Referring to FIGS. 6A-6E for example, the system 100 can utilize the registration of the second vertebra 659b as an initialization to register (e.g., locally register) preoperative image data of one or more of the first vertebra 659a, the third vertebra 659c, the fourth vertebra 659d, and/or other anatomical features.

Figure 7:
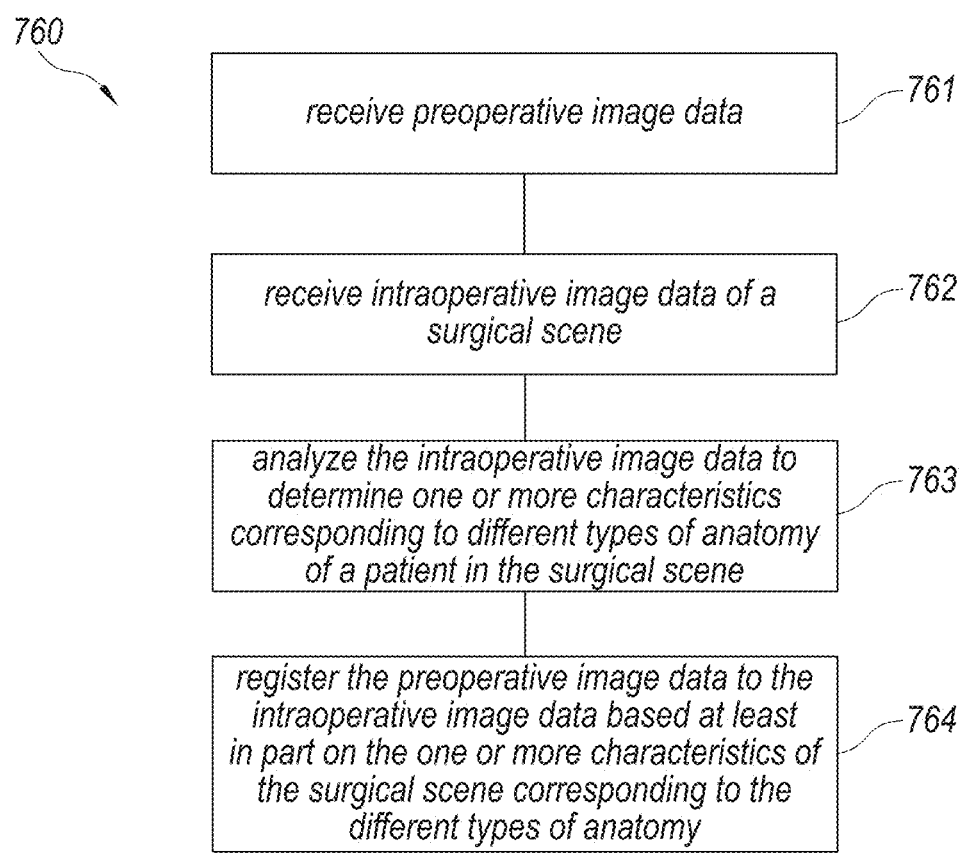
FIG. 7 is a flow diagram of a process or method for registering preoperative image data to intraoperative image data in accordance with additional embodiments of the present technology.

FIG. 7 is a flow diagram of a process or method 760 for registering preoperative image data to intraoperative image data in accordance with additional embodiments of the present technology. In some embodiments, the method 760 can be used to globally register and/or locally register the preoperative image data to the intraoperative image data at blocks 333 and 334 of the method 330 described in detail with reference to FIGS. 3-4C. Although some features of the method 760 are described in the context of the system 100 shown in FIGS. 1 and 2 for the sake of illustration, one skilled in the art will readily understand that the method 760 can be carried out using other suitable systems and/or devices described herein.

At block 761, the method 760 includes receiving preoperative image data. As described in detail above, the preoperative image data can comprise medical scan data representing a three-dimensional volume of a patient, such as computerized tomography CT scan data. At block 762, the method 760 includes receiving intraoperative image data of the surgical scene 108 from, for example, the camera array 110. As described in detail above, the intraoperative image data can include real-time or near-real-time images from the cameras 112 and/or the depth cameras 118 of the depth sensor 114, such as images of a patient's spine undergoing spinal surgery. In some embodiments, the intraoperative image data can include light-field data from the cameras 112.

Figure 8:
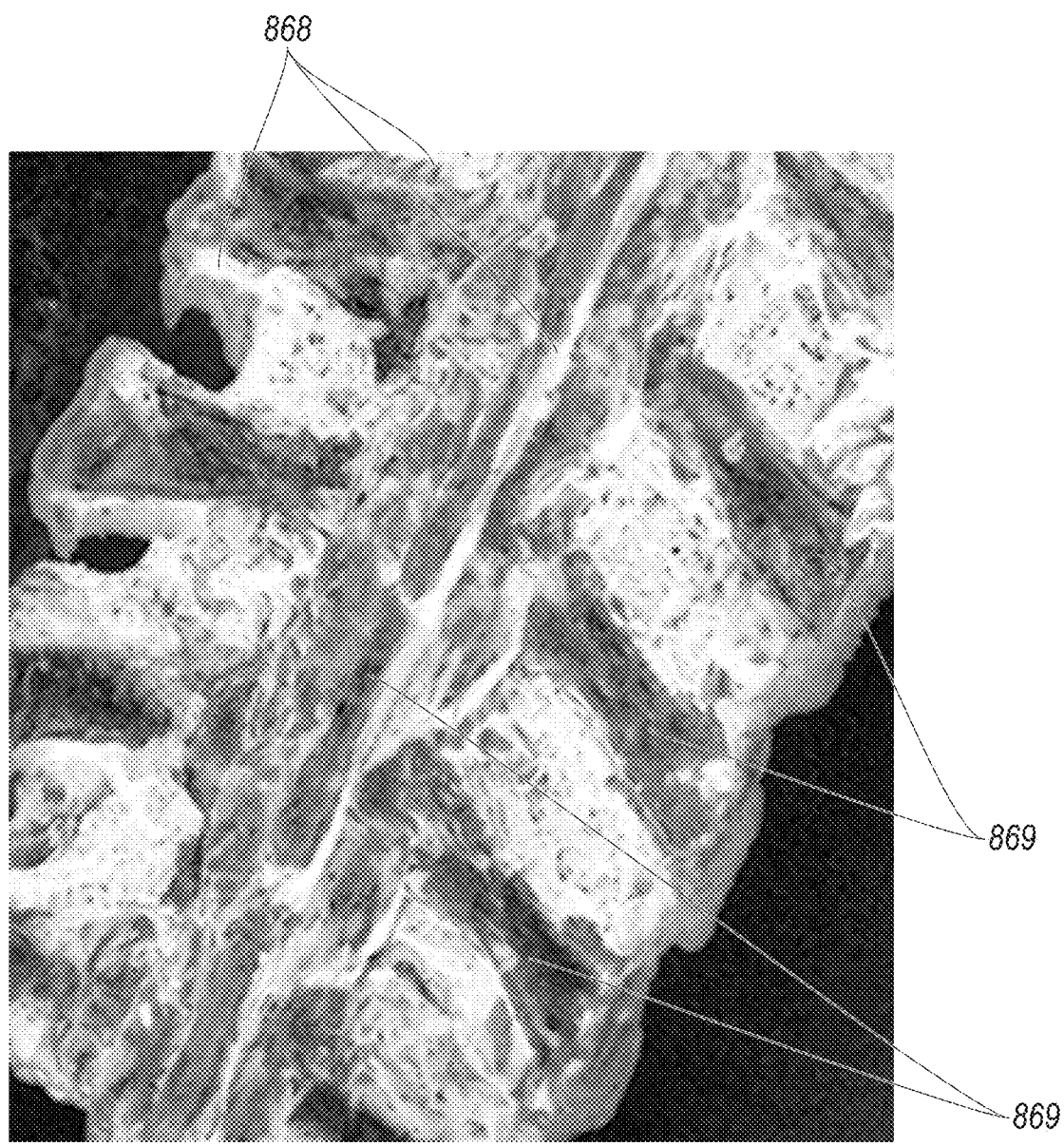
FIG. 8 is an image of a spine of a patient captured by the camera array of the imaging system of FIG. 1 in accordance with embodiments of the present technology.

At block 763, the method 760 includes analyzing the intraoperative image data to determine one or more characteristics/metrics corresponding to different types of anatomy of a patient in the surgical scene. For example, the registration processing device 105 can analyze light-field data (e.g., hyperspectral light-field data) from the cameras 112 such as color (e.g., hue, saturation, and/or value), angular information, and/or specular information to classify different portions of the anatomy of the patient as tissue, bone, ligament, tendon, nerve, and the like. FIG. 8, for example, is an image of a spine 868 of a patient captured by one or more of the cameras 112 in accordance with embodiments of the present technology. The spine 868 is formed from bone (e.g., a first type of anatomy) and is interspersed with and surrounded by other anatomical features such as flesh 869 (e.g., a second type of anatomy). In the illustrated embodiment, the intraoperative image data of the spine 868 has a lower saturation and higher brightness than the flesh 869. In some embodiments, one or more of the types of anatomy can correspond to the preoperative image data. That is, the preoperative image data can be of one or more of the types of anatomy in the intraoperative image data. For example, the image data of the spine 868 can correspond to preoperative image data including a CT scan or other medical scan of the spine 868.

At block 764, the method 760 includes registering the preoperative image data to the intraoperative image data based at least in part on the one or more characteristics corresponding to the different types of anatomy. For example, some registration algorithms (e.g., iterative closest point (ICP) algorithms) optionally include weights that can be applied on a point-by-point basis for each correspondence used to compute the registration transform—such as each correspondence between (i) a point cloud or mesh generated from the depth sensor 114 and (ii) a point cloud or mesh representing the preoperative image data. That is, the registration algorithm can apply individual weights to the correspondences between first points in the intraoperative image data and second points in the preoperative image data. In some embodiments, the weights of the registration algorithm can be adjusted based on the determined characteristics in the intraoperative image data corresponding to the anatomy of the patient (block 763). For example, for spinal procedures, it is often desired to register CT data of the spine to intraoperative images of the patient's exposed spine during the procedure. Accordingly, with reference to FIG. 8, if a particular point (e.g., a point in a point cloud from the depth sensor 114) is mapped to a pixel captured by the cameras 112 having a characteristic indicating that is likely a part of the spine 868—such as a relatively low saturation, high brightness, and/or the like—the weight for the correspondence for that point in the registration algorithm can be increased. Conversely, if the image data from the cameras 112 indicates that a point is likely a part of the flesh 869 or other anatomy, the weight for that point can be decreased. In some embodiments, the weights assigned to the correspondences between points can be a learned and/or tuned function of the light-field characteristics for the points—such as a combination of hue, saturation, color, angular, and/or specular information. In contrast, typical approaches determine the weights for registration algorithms from scene-agnostic metrics that are derived solely from the structure (e.g., local structure) of the point cloud or mesh used for registration.

In some aspects of the present technology, using the light-field image data from the cameras 112 to create weights for the registration transform still allows flesh, blood, and/or other anatomical features close to the surface of the spine 868 to be included in and provide positive input to the registration. In some embodiments, the weights for certain points can be binary (e.g., fully weighted or not included) based on the light-field characteristics for that point. For example, points indicated to be along the spine 868 can be weighted with a "1" while points indicated to be along the flesh 869 can be weighted with a "0". Accordingly, in some embodiments the method 760 operates to segment out portions of the intraoperative image data (e.g., portions of bone) for registration thereby increasing the accuracy of registration.

Figure 9:
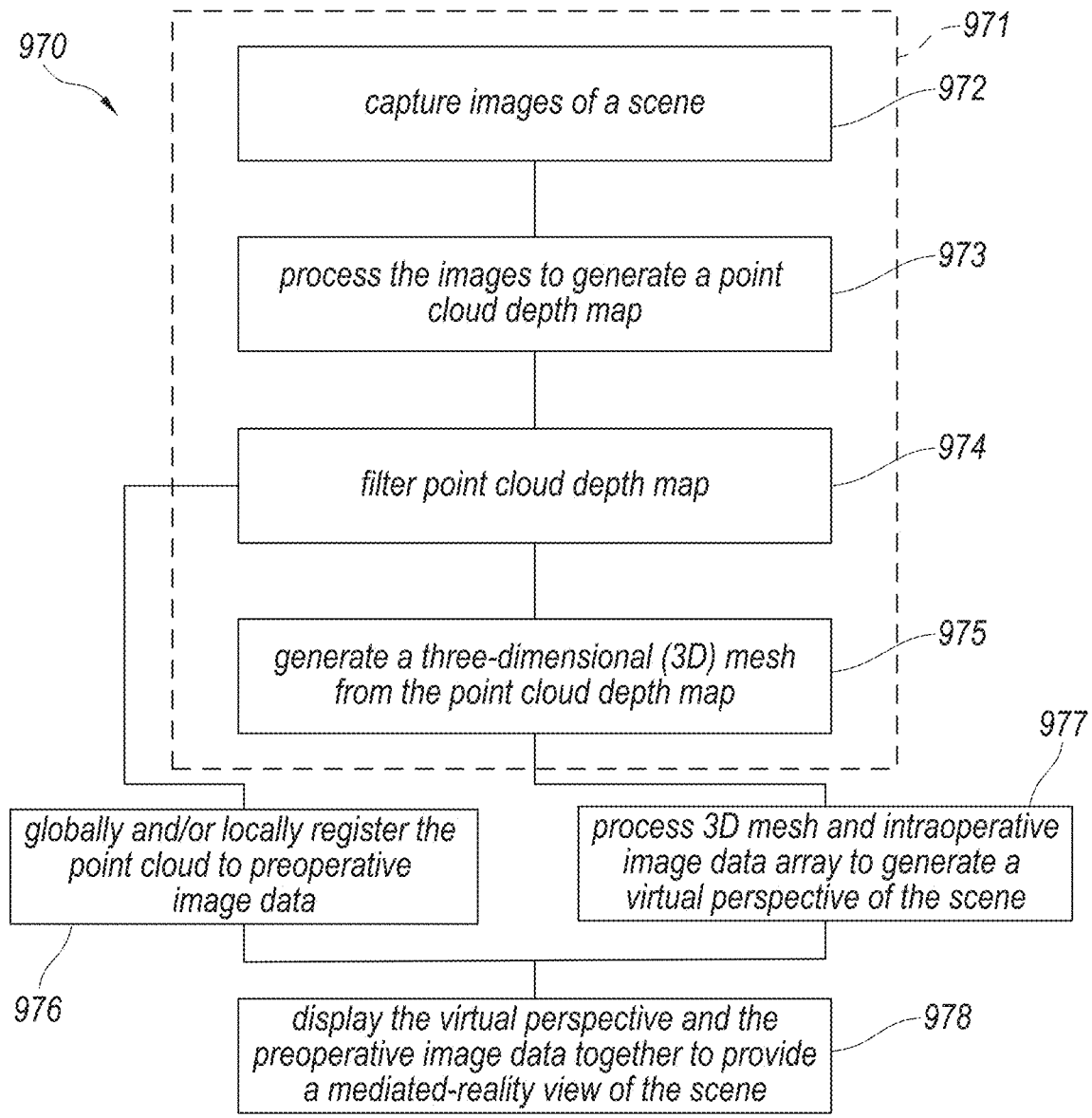
FIG. 9 is a flow diagram of a process or method for registering preoperative image data to intraoperative image data to generate a mediated reality view of a surgical scene in accordance with additional embodiments of the present technology.

FIG. 9 is a flow diagram of a process or method 970 for registering preoperative image data to intraoperative image data to generate a mediated reality view of a surgical scene in accordance with additional embodiments of the present technology. Although some features of the method 970 are described in the context of the system 100 shown in FIGS. 1 and 2 for the sake of illustration, one skilled in the art will readily understand that the method 970 can be carried out using other suitable systems and/or devices described herein.

At combined block 971, the method 970 includes receiving intraoperative image data of the scene 108 and processing the intraoperative image data to generate depth information. More specifically, at block 972, the method includes capturing images of the scene 108 with the depth cameras 118 of the depth sensor 114. In some embodiments, the images are stereo images of the scene 108 including depth information from, for example, a pattern projected into/onto the scene by the projector 116. In some embodiments, the depth sensor 114 has a resolution that is the same as or about the same as the preoperative image data.

At block 973, the method 970 includes processing the images to generate a point cloud depth map. For example, the processing device 102 (e.g., the image processing device 103 and/or the registration processing device 105) can process the image data from the depth sensor 114 to estimate a depth for each surface point of the scene 108 relative to a common origin and to generate a point cloud that represents the surface geometry of the scene 108. In some embodiments, the processing device 102 can utilize a semi-global matching (SGM), semi-global block matching (SGBM), and/or other computer vision or stereo vision algorithm to process the image data to generate the point cloud. In some embodiments, the point cloud can have a have a range density of one point per 0.11 square millimeters (9 pt/mm$^2$) to one point per nine square millimeters (0.11 pt/mm$^2$)

At block 974, the method 970 can optionally include filtering the point cloud depth map to, for example, remove outliers (e.g., using a median or weighted analysis). At block 975, the method includes generating a 3D mesh from the point cloud depth map. In some embodiments, the processing device 102 can generate the 3D mesh using a marching cubes or other suitable algorithm. In some embodiments, generating the 3D mesh can take about 25% or greater of the total time to execute the combined block 971.

At block 976, the method 970 includes globally and/or locally registering the point cloud to preoperative image data. In some embodiments, the global and/or local registration can utilize any of the registration methods/techniques described in detail above with reference to FIGS. 3-8. In some embodiments, utilizing the lower density/resolution point cloud—instead of the greater density 3D mesh—is sufficient to achieve accurate registration. Accordingly, in the illustrated embodiment the global and/or local registration proceeds from block 974 and utilizes the filtered point cloud for registration to the preoperative image data. In some aspects of the present technology, using the point cloud rather than the 3D mesh requires less data analysis and thus results in faster registration processing. For example, utilizing a point cloud having a 0.11 pt/mm$^2$ density rather than a 3D mesh having a 9 pt/mm$^2$ density can result in an 81 times reduction in data usage.

At block 977, the method 970 includes processing the 3D mesh and image data from the cameras 112 of the camera array 110 to generate/synthesize a virtual perspective of the scene 108, as described in detail above with reference to FIG. 1. In some aspects of the present technology, because the registration process (block 976) utilizes the point cloud rather the 3D mesh, the registration process can be initialized and begin to run before and during the virtual synthesis of the perspective of the scene (block 977). That is, these processes can be run in parallel—increasing the processing speed of the method 970.

At block 978, the method 970 includes displaying the virtual perspective and the registered preoperative image data together (e.g., on the display device 104) to provide a mediated-reality view of the scene 108 to a user. In some embodiments, blocks 976-978 of the method 970 can operate generally similarly or identically to, for example, blocks 332-337 of the method 330 described in detail with reference to FIGS. 3-4C.

Figure 10:
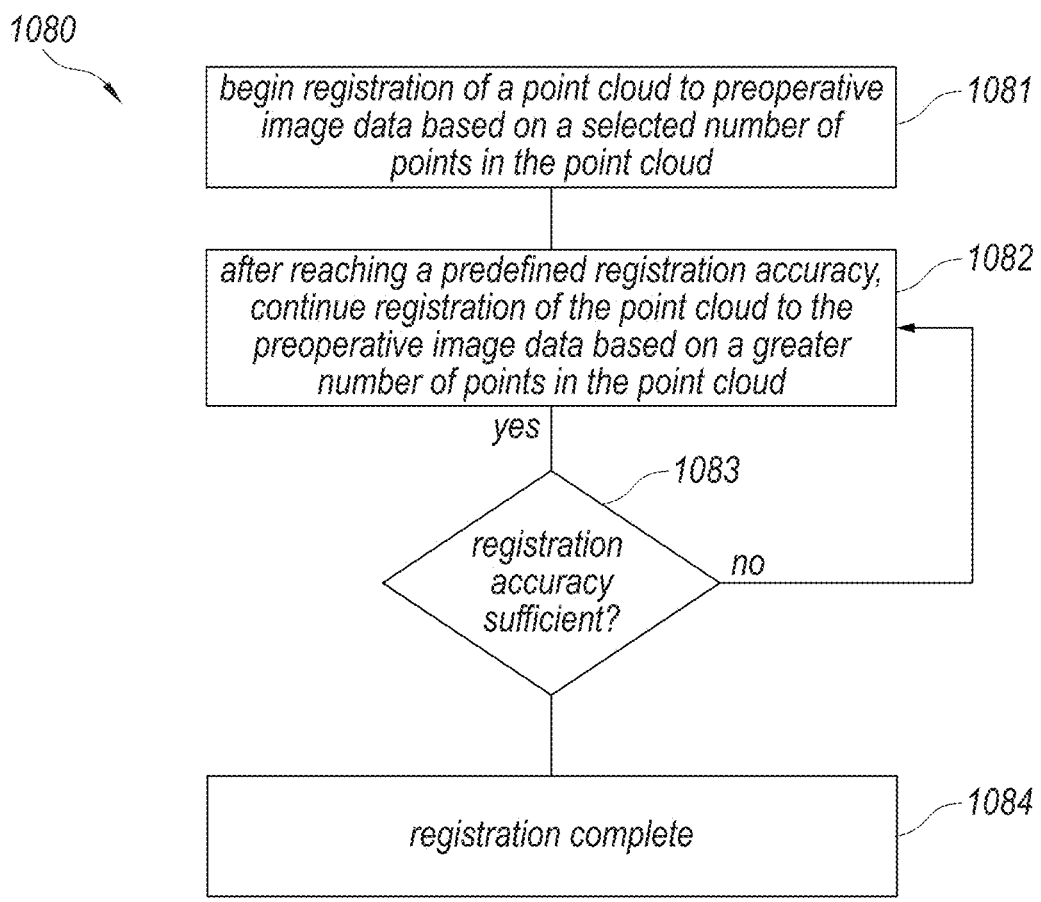
FIG. 10 is a flow diagram of a process or method for registering a point cloud depth map of a scene to preoperative image data of a portion of the scene in accordance with embodiments of the present technology.
Figure 11:
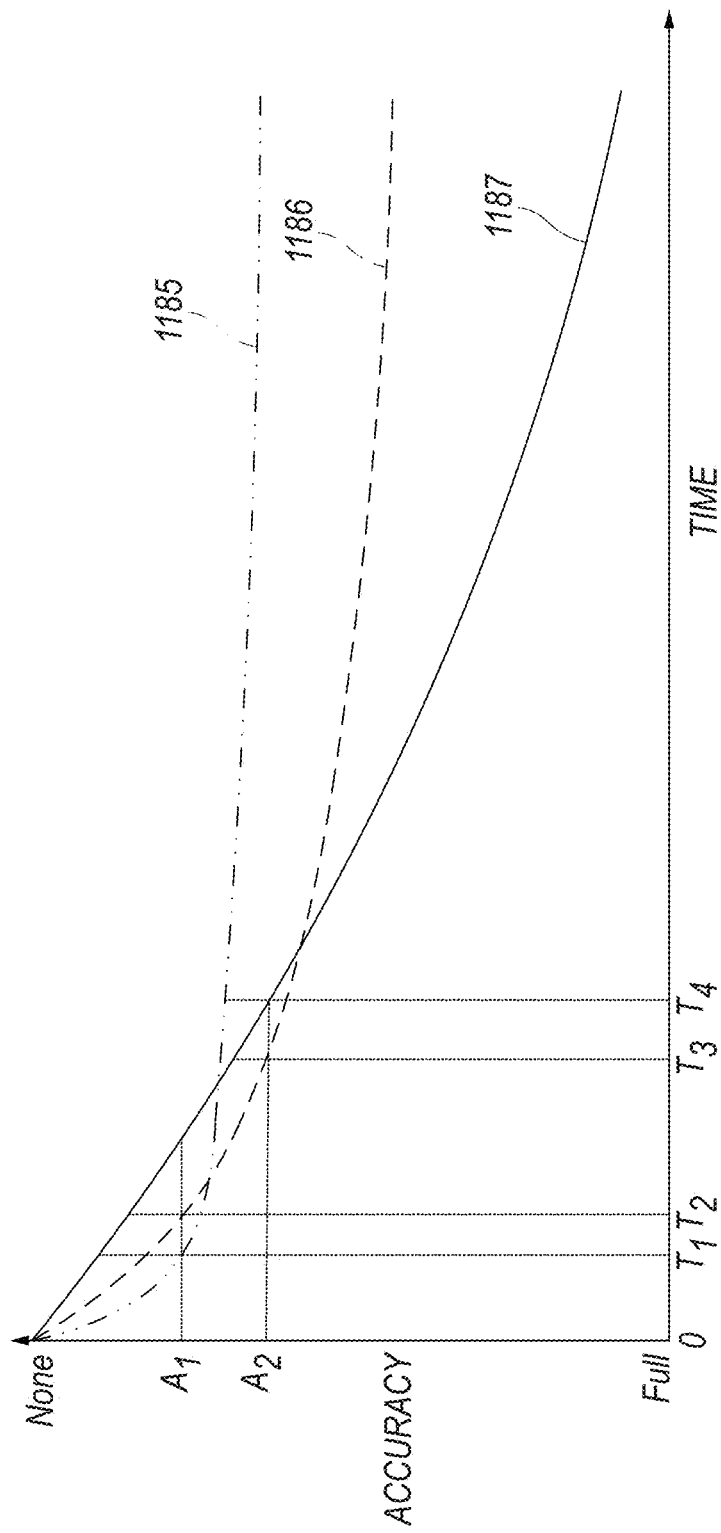
FIG. 11 is a graph of an accuracy of a registration algorithm over time for the processing of different numbers/densities of points in a point cloud in accordance with embodiments of the present technology.

FIG. 10 is a flow diagram of a process or method 1080 for registering a point cloud depth map of a scene to preoperative image data of a portion of the scene in accordance with embodiments of the present technology. In some embodiments, the method 1080 can be used to locally and/or globally register the point cloud to the preoperative image data at block 976 of the method 970 described in detail with reference to FIG. 9. FIG. 11 is a graph of the accuracy of a registration algorithm over time for the processing of different numbers/densities of points in the point cloud in accordance with embodiments of the present technology. In the illustrated embodiment, a first curve 1185 represents the processing of a first number of points (e.g., 10% of the total points in the point cloud), a second curve 1186 represents the processing of a second number of points greater than the first number of points (e.g., 50% of the total points in the point cloud), and a third curve 1187 represents the processing of a third number of points greater than the first number of points (e.g., 100% of the total points in the point cloud).

Referring to FIGS. 10 and 11 together, at block 1081 the method 1080 includes beginning to register the point cloud to the preoperative image data based on a selected number of points in the point cloud. For example, registration can begin by running a selected registration algorithm (e.g., an ICP algorithm) based on the first number of points represented by the first curve 1185. As shown in FIG. 11, processing of the first number of points can reach a first selected accuracy $A_1$ at a time $T_1$ that is earlier than the processing of the second or third number of points represented by the second and third curves 1186 and 1187, respectively, reaches the accuracy $A_1$. That is, processing fewer points can achieve a first level of accuracy more quickly than processing a greater number of points.

However, the first curve 1185 quickly flattens out at a relatively low accuracy. Accordingly, at block 1082 the method 1080 can include, after reaching a predefined registration accuracy level (and/or a predefined processing time), continuing registration of the point cloud to the preoperative image data based on a greater number of points in the point cloud. For example, registration can continue by running the selected registration algorithm based on the second number of points represented by the second curve 1186 after the initial processing of the first number of points represented by the first curve 1185 reaches the first selected accuracy $A_1$. Therefore, processing of the second number of points can effectively begin (e.g., be initialized) at the time $T_1$ at the first selected accuracy level $A_1$—which would not be reached by processing of the second number of points alone until the time $T_2$. Accordingly, by first processing the fewer first number of points before switching to processing the greater second number of points at the accuracy level $A_1$, the processing time of the registration algorithm can be reduced by the difference between the times $T_1$ and $T_2$ (i.e., the time $T_2$-$T_1$)—increasing the overall processing speed.

At decision block 1083, the method 1080 includes determining whether a sufficient registration accuracy has been reached. If yes, the method 1080 can proceed to end at block 1084 with the registration complete. If no, the method 1080 can return to block 1082 and, after reaching another predefined registration accuracy level (and/or a predefined processing time), continue registration of the point cloud to the preoperative image data based on a greater number of points in the point cloud. For example, registration can continue by running the selected registration algorithm based on the third number of points represented by the third curve 1187 after the processing of the second number of points represented by the second curve 1186 reaches a second selected accuracy $A_2$ at a time $T_3$. Therefore, processing of the third number of points is initialized at the time $T_3$ at the second selected accuracy level $A_2$—which would not be reached by processing of the third number of points alone until the time $T_4$. Accordingly, by first processing the fewer second number of points before switching to processing the greater third number of points at the accuracy level $A_2$, the processing time of the registration algorithm can be reduced by the difference between the times $T_3$ and $T_4$ (i.e., the time $T_4$-$T_2$)—increasing the overall processing speed. The method 1080 can return to block 1082 any number of times to differentially process different numbers of points in the point cloud in, for example, a stepped fashion.

Figure 12:
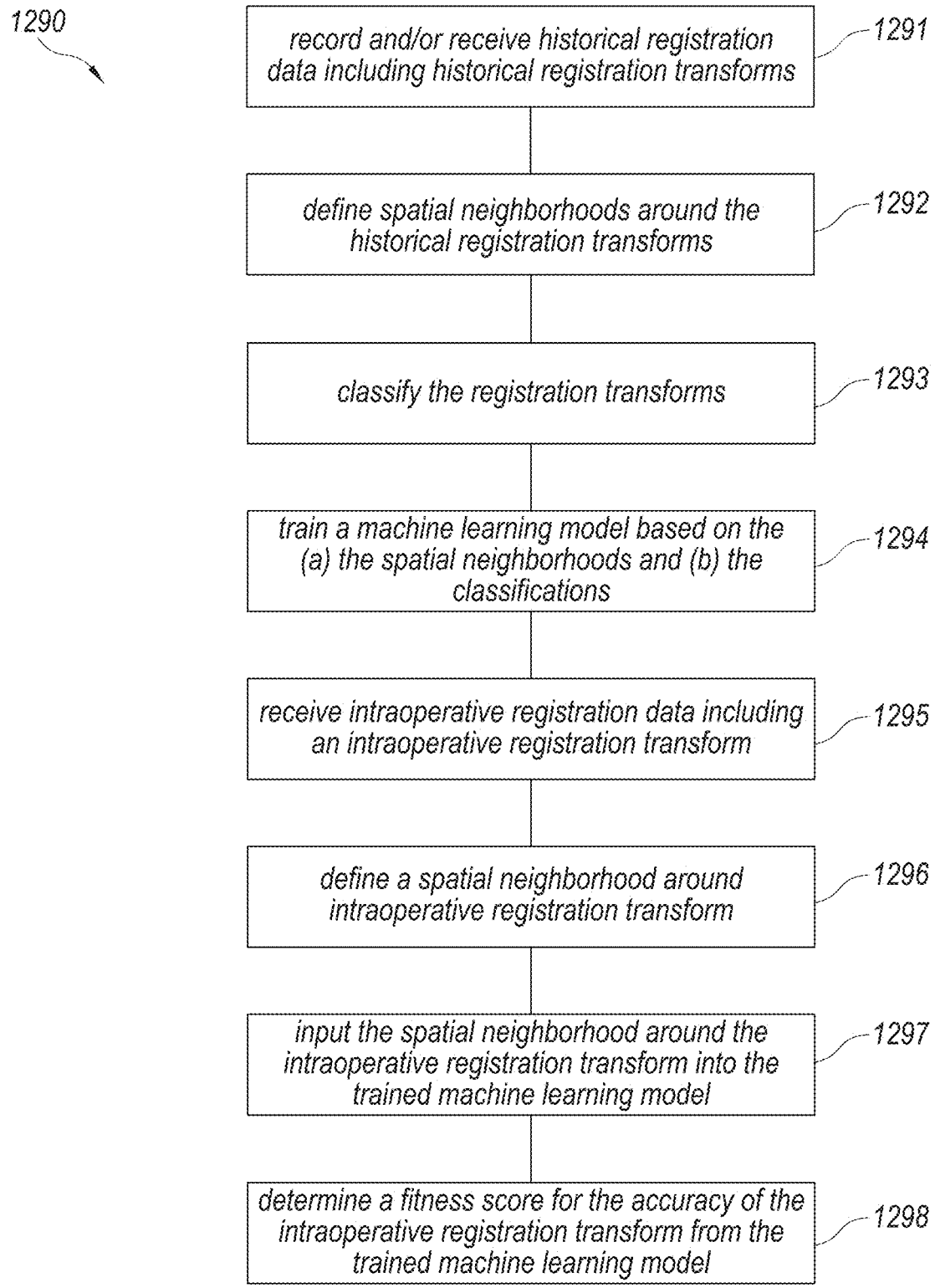
FIG. 12 is a flow diagram of a process or method for determining an accuracy of a registration between intraoperative image data and preoperative image data in accordance with embodiments of the present technology.

FIG. 12 is a flow diagram of a process or method 1290 for determining an accuracy of a registration—such as a global and/or local registration—between intraoperative image data and preoperative image data in accordance with embodiments of the present technology. Although some features of the method 1290 are described in the context of the system 100 shown in FIGS. 1 and 2 for the sake of illustration, one skilled in the art will readily understand that the method 1290 can be carried out using other suitable systems and/or devices described herein.

At block 1291, the method 1290 includes recording and/or receiving historical registration data. The historical registration data can include, for example, example data sets including (i) preoperative image data (e.g., a 3D data set such as CT scan data), (ii) intraoperative image data (e.g., a 3D point cloud or mesh derived from the depth sensor 114), and (iii) a registration transform for mapping the preoperative image data to the intraoperative image data. In some embodiments, the example data sets can be recorded/compiled from previous surgical procedures and/or can be generated as test cases. In some embodiments, the registration transforms can be calculated using any of the methods described in detail above with reference to FIGS. 3-11.

At block 1292, the method 1290 includes defining spatial neighborhoods around the historical registration transforms. The spatial neighborhoods can include slight variations/deviations in the values of the historical registration transforms, such as small translational, rotational, and/or reflective variations. In some embodiments, the spatial neighborhoods can be feature vectors (e.g., 729×1 feature vectors) that are generated by transforming the historical preoperative image data (e.g., source data) and/or the historical intraoperative image data to neighboring poses in the special Euclidean group space (SE(n)). In some embodiments, the neighboring poses can be within a threshold rotational and translational variance, such as within about ±5 degrees rotationally and about ±0.3 millimeters translationally.

At block 1293, the method 1290 includes classifying/labeling the historical registration transforms. For example, each of the historical registration transforms and corresponding spatial neighborhood can be classified with a binary label as a "good" or "accurate" transform or a "bad" or "inaccurate" transform based on predefined criteria. In some embodiments, the predefined criteria can be selected acceptable deviations from a true registration (e.g., a 100% accurate registration). For example, "good" transforms can be defined to be within a selected rotational variance (e.g., ±1 degree) and translational variance (e.g., ±0.5 millimeter) from the true registration. In some embodiments, to generate "bad" transforms, random noise in translation and rotation can be introduced into some or all of the "good" historical registration transforms.

At block 1294, the method 1290 includes training a machine learning model based on (i) the spatial neighborhoods around the historical registration transforms and (ii) the classifications for those transforms. More specifically, for each of the examples of historical registration data, the machine learning algorithm can be trained with a feature vector representing the neighborhood around the historical registration transform and an associated binary label. In some embodiments, the machine learning algorithm can be a singular value decomposition (SVD) or neural network. In other embodiments, other machine learning techniques may be employed. Such machine learning techniques include a support vector machine, a Bayesian network, learning regression, and/or a neural network, when generating weights. A support vector machine may be trained using examples of good registration transforms and bad registration transforms as training data. A support vector machine operates by finding a hypersurface in the space of possible inputs. The hypersurface attempts to split the positive examples (i.e., good registration transforms) from the negative examples (i.e., bad registration transforms) by maximizing the distance between the nearest of the positive and negative examples and the hypersurface. A support vector machine simultaneously minimizes an empirical classification error and maximizes a geometric margin. This allows for correct classification of data that is similar to but not identical to the training data. Various techniques can be used to train a support vector machine. Some techniques use a sequential minimal optimization algorithm that breaks the large quadratic programming problem down into a series of small quadratic programming problems that can be solved analytically.

At block 1295, the method 1290 includes receiving intraoperative registration data including an intraoperative registration transform. Similar to the historical registration data, the intraoperative registration data can include, for example, a data set including (i) preoperative image data (e.g., a 3D data set such as CT scan data), (ii) intraoperative image data (e.g., a 3D point cloud or mesh derived from the depth sensor 114), and (iii) a registration transform for mapping the preoperative image data to the intraoperative image data. Such intraoperative registration data can be obtained using any of the techniques described in detail above with reference to FIGS. 3-11.

At block 1296, the method 1290 includes defining a spatial neighborhood around the intraoperative registration transform. Similar to the neighborhoods around the historical registration transforms, the spatial neighborhood around the intraoperative registration transform can be a feature vector defining a set of neighboring poses or transforms around the determined intraoperative registration transform.

At block 1297, the method 1290 includes inputting the spatial neighborhood around the intraoperative registration transform into the trained machine learning model. Based on the input, at block 1298, the method 1290 includes determining a fitness score for the accuracy of the intraoperative registration transform. The fitness score can be a binary "good' or "bad" determination or can be a score along a continuous or more discrete spectrum. In some embodiments, if the fitness score is below a predetermined threshold, the system 100 can attempt to reregister the preoperative image data to the intraoperative image data. In some aspects of the present technology, evaluating the neighborhood of values of around a given registration transform—rather than the transform alone—increases the confidence in the evaluation of registration accuracy.

The methods 330, 550, 760, 970, 1080, and 1290 described in detail above with reference to FIGS. 3-12 can include some features generally similar to and/or operate generally similarly to one another. For example, the various stages of the methods can be combined with one another, omitted, and/or practiced in a different order. Moreover, while reference throughout has been made to preoperative image data and intraoperative image data, these data sources can be of other types without deviating from the scope of the present technology. For example, preoperative image data and/or intraoperative image data can include depth data from sources other than cameras imaging a scene.

III. ADDITIONAL EXAMPLES

The following examples are illustrative of several embodiments of the present technology:

1. A method of registering medical scan data of a patient to intraoperative image data of a scene including the patient, the method comprising:

generating a three-dimensional (3D) image of the scene based on the intraoperative image data, wherein the medical scan data corresponds to a portion of the patient at least partially visible in the 3D image;

overlaying the medical scan data over the 3D image;

receiving a user input to move the medical scan data into alignment with the portion of the patient in the 3D image; and registering the medical scan data to the portion of the patient in the 3D image based on the alignment.

2. The method of example 1 wherein the method further comprises continuously receiving the intraoperative image data, and wherein generating the 3D image includes continuously updating the virtual image based on the intraoperative image data.

3. The method of example 1 or example 2 wherein the method further comprises displaying the 3D image and the medical scan data on a display device in substantially real-time as perceived by a user of the display device.

4. The method of any one of examples 1-3 wherein the medical scan data is a segmented portion of a computerized tomography (CT) scan.

5. The method of any one of examples 1-4 wherein the medical scan data is of a vertebra of the patient, and wherein the portion of the patient in the 3D image is a spine of the patient.

6. The method of any one of examples 1-5 wherein registering the medical scan data includes globally registering the medical scan data to the portion of the patient in the 3D image, and wherein the method further comprises locally registering the medical scan data to the portion of the patient in the 3D image based at least in part on the global registration.

7. The method of example 6 wherein the method further comprises, after locally registering the medical scan data to the portion of the patient in the 3D image, automatically moving the medical scan data into further alignment with the portion of the patient in the 3D image.

8. The method of any one of examples 1-7 wherein the user input is from a tool movable through the scene.

9. The method of example 8 wherein overlaying the medical scan data over the 3D image includes displaying the medical scan data at a tip of the tool in the scene.

10. The method of any one of examples 1-9 wherein the user input is to drag the medical scan data toward the portion of the patient in the 3D image.

11. The method of any one of examples 1-10 wherein the user input is to rotate the medical scan data toward the portion of the patient in the 3D image.

12. A mediated-reality system, comprising:
a camera array including a plurality of cameras configured to capture intraoperative image data of a scene including a patient;
an input controller configured to control a position and orientation of a virtual perspective of the scene;
a processing device communicatively coupled to the camera array and the input controller, wherein the processing device is configured to—
synthesize a virtual image corresponding to the virtual perspective based on the intraoperative image data;
receive medical scan data of the patient corresponding to a portion of the patient at least partially visible in the virtual image;
overlay the medical scan data over the virtual image;
receive a user input to move the medical scan data into alignment with the portion of the patient in the virtual image; and
register the medical scan data to the portion of the patient in the virtual image based on the alignment.

13. The mediated-reality system of example 12, further comprising a display device communicatively coupled to the processing device, wherein the display device is configured to display a three-dimensional (3D) graphical representation of the medical scan data over the virtual image.

14. The mediated-reality system of example 12 or example 13, further comprising a tool communicatively coupled to the processing device, wherein the user input is based on a position of the tool relative to the scene.

15. The mediated-reality system of example 14 wherein the user input is a physical translation, a physical rotation, or both a physical translation and a physical rotation of the tool relative to the scene.

16. The mediated-reality system of any one of examples 12-15 wherein the scene is a surgical scene, wherein the portion of the patient at in the virtual image includes a spine of the patient, and wherein the medical scan data is computerized tomography (CT) scan data.

17. A method of registering previously-captured image data to real-time image data of a scene, the method comprising:
generating a three-dimensional (3D) virtual view of the scene based on the real-time image data, wherein the scene includes an object of interest, and wherein the previously-captured image data corresponds to the object of interest;
displaying the 3D virtual view on a display device visible to a user;
displaying the previously-captured image data on the display device over the 3D virtual view;
receiving user input to move the previously-captured image data relative to the 3D virtual view such that the previously-captured image data is at least partially aligned with the object of interest in the 3D virtual view; and
generating a registration transform between the previously-captured image data and the object of interest in the 3D virtual view based on the alignment of the previously-captured image data and the object of interest in the 3D virtual view.

18. The method of example 17 wherein displaying the 3D virtual view on the display device includes displaying the 3D virtual view in substantially real-time as perceived by the user.

19. The method of example 17 or example 18 wherein the method further comprises:
locally registering the previously-captured image data to the object of interest in the 3D virtual view based at least in part on the registration transform; and
automatically moving the previously-captured image data into further alignment with the object of interest in the 3D virtual view based on the local registration.

20. The method of any one of examples 17-19 wherein the user input is based on a position of the tool relative to the scene, wherein displaying the previously-captured image data over the 3D virtual view includes displaying a 3D representation of the previously-captured image data in the 3D virtual view at a position corresponding to a tip of the tool in the scene, and wherein the user input is a physical movement of the tool through the scene.

21. A method of registering medical scan data of a patient to intraoperative image data of a scene including the patient, the method comprising:
determining one or more characteristics of the intraoperative image data;
based on the determined one or more characteristics, determining that (a) a first portion of the intraoperative image data corresponds to a first type of anatomy the patient and (b) a second portion of the intraoperative image data corresponds to a second type of anatomy of the patient, wherein the first type of anatomy corresponds to the medical scan data; and registering the preoperative image data to the first portion of the intraoperative image data.

22. The method of example 21 wherein the preoperative image data is computerized tomography (CT) scan data.

23. The method of example 21 or example 22 wherein the first type of anatomy is bone.

24. The method of any one of examples 21-23 wherein registering the preoperative image data to the first portion of the intraoperative image data includes— utilizing a registration algorithm to compute a registration transform between the preoperative image data and the first portion of the intraoperative image data; and adjusting the registration algorithm based on the determined one or more characteristics.

25. The method of example 24 wherein utilizing the registration algorithm includes computing a plurality of point-to-point correspondences between first points in the intraoperative image data and second points in the preoperative image data, and wherein adjusting the registration algorithm includes adjusting weights of the point-to-point correspondences based on a determination that the first points in the point-to-point correspondences correspond to the first type of anatomy or the second type of anatomy.

26. The method of example 25 wherein adjusting the weights of the point-to-point correspondences includes (a) increasing the weights of ones of the point-to-point correspondences including first points corresponding to the first type of anatomy and (b) decreasing weights of ones of the point-to-point correspondences including first points corresponding to the second type of anatomy.

27. The method of any one of examples 21-26 wherein the one or more characteristics include at least one of color information, angular information, and specular information.

28. The method of any one of examples 21-27 wherein the one or more characteristics include at least one of hue, saturation, and value information.

29. The method of any one of examples 21-28 wherein the intraoperative image data includes light-field image data of the scene.

30. The method of example 29 wherein the intraoperative image data further includes image data from a depth camera including depth data of the scene, wherein determining the one or more characteristics of the image data includes determining the one or more characteristics based on the light-field image data, and wherein registering the preoperative image data to the first portion of the intraoperative image data includes registering the depth data to the preoperative image data.

31. The method of any one of examples 21-30 wherein the method further comprises:

generating a three-dimensional (3D) image of the scene based on the intraoperative image data; and displaying the medical scan data over the first type of anatomy in the 3D image of the scene.

32. A mediated-reality system, comprising:

a camera array including a plurality of cameras configured to capture intraoperative image data of a scene including a patient;

an input controller configured to control a position and orientation of a virtual perspective of the scene;

a processing device communicatively coupled to the camera array and the input controller, wherein the processing device is configured to— synthesize a virtual image corresponding to the virtual perspective based on the intraoperative image data;

receive medical scan data of the patient;

determine one or more characteristics of the intraoperative image data;

based on the determined one or more characteristics, determine that (a) a first portion of the intraoperative image data corresponds to a first type of anatomy the patient and (b) a second portion of the intraoperative image data corresponds to a second type of anatomy of the patient, wherein the first type of anatomy corresponds to the medical scan data;

register the preoperative image data to the first portion of the intraoperative image data; and overlay the medical scan data over the first type of anatomy in the virtual image.

33. The mediated-reality system of example 32 wherein the scene is a surgical scene, wherein the first type of anatomy is a spine of the patient, and wherein the medical scan data is computerized tomography (CT) scan data.

34. The mediated-reality system of example 32 or example 33 wherein the one or more characteristics include at least one of hue, saturation, and value information, and wherein the intraoperative image data includes light-field image data of the scene.

35. The mediated-reality system of any one of examples 32-34 wherein the processor is configured to register the preoperative image data to the first portion of the intraoperative image data by— utilizing a registration algorithm to compute a plurality of point-to-point correspondences between first points in the intraoperative image data and second points in the preoperative image data; and adjusting weights of the point-to-point correspondences based on the determination that the first points in the point-to-point correspondences correspond to the first type of anatomy or the second type of anatomy.

36. The mediated-reality system of any one of examples 32-35 wherein the processor is further configured to adjust the weights of the point-to-point correspondences by (a) increasing the weights of ones the point-to-point correspondences including first points corresponding to the first type of anatomy and (b) decreasing the weights of ones of the point-to-point correspondences including first points corresponding to the second type of anatomy.

37. A method of registering previously-captured image data to real-time image data of a scene, the method comprising:

receiving the real-time image data including light-field image data of the scene;

generating a three-dimensional (3D) virtual view of the scene based on the real-time image data, wherein the scene includes an object of interest, and wherein the previously-captured image data corresponds to the object of interest;

determining one or more characteristics of the light-field image data;

based on the determined one or more characteristics, determining that (a) a first portion of the real-time image data likely corresponds to the object of interest and (b) a second portion of the real-time image data likely does not correspond to the object of interest;

registering the previously-captured image data to the first portion of the real-time image data; and displaying the previously-captured image data over the object of interest in the 3D virtual view of the scene.

38. The method of example 37 wherein the one or more characteristics include at least one of color information, angular information, and specular information.

39. The method of example 37 or example 38 wherein registering the previously-captured image data to the first portion of the real-time image data includes—
utilizing a registration algorithm to compute a plurality of point-to-point correspondences between first points in the real-time image data and second points in the previously-captured image data; and
adjusting weights of the point-to-point correspondences based on the determination that the first points in the point-to-point correspondences likely correspond to the object of interest.

40. The method of any one of examples 37-39 wherein determining that the first portion of the real-time image data likely corresponds to the object of interest includes determining that the light-field image data corresponding to the first portion of the real-time image data has a lower saturation than other portions of the light-field image data.

IV. CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of registering medical scan data of a patient to intraoperative image data of a scene including the patient, the method comprising:
determining one or more characteristics of the intraoperative image data;
based on the determined one or more characteristics, determining that (a) a first portion of the intraoperative image data corresponds to a first type of anatomy the patient and (b) a second portion of the intraoperative image data corresponds to a second type of anatomy of the patient, wherein the first type of anatomy corresponds to the medical scan data; and
registering the preoperative image data to the first portion of the intraoperative image data, wherein registering the preoperative image data to the first portion of the intraoperative image data includes—
utilizing a registration algorithm to compute a registration transform between the preoperative image data and the first portion of the intraoperative image data, wherein utilizing the registration algorithm includes computing a plurality of point-to-point correspondences between first points in the intraoperative image data and second points in the preoperative image data; and
adjusting the registration algorithm based on the determined one or more characteristics, wherein adjusting the registration algorithm includes adjusting weights of the point-to-point correspondences based on a determination that the first points in the point-to-point correspondences correspond to the first type of anatomy or the second type of anatomy.

2. The method of claim 1 wherein the preoperative image data is computerized tomography (CT) scan data.

3. The method of claim 1 wherein the first type of anatomy is bone.

4. The method of claim 1 wherein adjusting the weights of the point-to-point correspondences includes (a) increasing the weights of ones of the point-to-point correspondences including first points corresponding to the first type of anatomy and (b) decreasing weights of ones of the point-to-point correspondences including first points corresponding to the second type of anatomy.

5. The method of claim 1 wherein the one or more characteristics include at least one of color information, angular information, and specular information.

6. The method of claim 1 wherein the one or more characteristics include at least one of hue, saturation, and value information.

7. The method of claim 1 wherein the intraoperative image data includes light-field image data of the scene.

8. The method of claim 7 wherein the intraoperative image data further includes image data from a depth camera including depth data of the scene, wherein determining the one or more characteristics of the image data includes determining the one or more characteristics based on the light-field image data, and wherein registering the preoperative image data to the first portion of the intraoperative image data includes registering the depth data to the preoperative image data.

9. The method of claim 1 wherein the method further comprises:
generating a three-dimensional (3D) image of the scene based on the intraoperative image data; and
displaying the medical scan data over the first type of anatomy in the 3D image of the scene.

10. A mediated-reality system, comprising:
a camera array including a plurality of cameras configured to capture intraoperative image data of a scene including a patient;

an input controller configured to control a position and orientation of a virtual perspective of the scene;

a processing device communicatively coupled to the camera array and the input controller, wherein the processing device is configured to— synthesize a virtual image corresponding to the virtual perspective based on the intraoperative image data;

receive medical scan data of the patient;

determine one or more characteristics of the intraoperative image data;

based on the determined one or more characteristics, determine that (a) a first portion of the intraoperative image data corresponds to a first type of anatomy the patient and (b) a second portion of the intraoperative image data corresponds to a second type of anatomy of the patient, wherein the first type of anatomy corresponds to the medical scan data;

register the preoperative image data to the first portion of the intraoperative image data by— utilizing a registration algorithm to compute a plurality of point-to-point correspondences between first points in the intraoperative image data and second points in the preoperative image data; and adjusting weights of the point-to-point correspondences based on the determination that the first points in the point-to-point correspondences correspond to the first type of anatomy or the second type of anatomy; and overlay the medical scan data over the first type of anatomy in the virtual image.

11. The mediated-reality system of claim 10 wherein the scene is a surgical scene, wherein the first type of anatomy is a spine of the patient, and wherein the medical scan data is computerized tomography (CT) scan data.

12. The mediated-reality system of claim 10 wherein the one or more characteristics include at least one of hue, saturation, and value information, and wherein the intraoperative image data includes light-field image data of the scene.

13. The mediated-reality system of claim 10 wherein the processor is further configured to adjust the weights of the point-to-point correspondences by (a) increasing the weights of ones the point-to-point correspondences including first points corresponding to the first type of anatomy and (b) decreasing the weights of ones of the point-to-point correspondences including first points corresponding to the second type of anatomy.

14. A method of registering previously-captured image data to real-time image data of a scene, the method comprising:

receiving the real-time image data including light-field image data of the scene;

generating a three-dimensional (3D) virtual view of the scene based on the real-time image data, wherein the scene includes an object of interest, and wherein the previously-captured image data corresponds to the object of interest;

determining one or more characteristics of the light-field image data;

based on the determined one or more characteristics, determining that (a) a first portion of the real-time image data likely corresponds to the object of interest and (b) a second portion of the real-time image data likely does not correspond to the object of interest;

registering the previously-captured image data to the first portion of the real-time image data, wherein registering the previously-captured image data to the first portion of the real-time image data includes— utilizing a registration algorithm to compute a plurality of point-to-point correspondences between first points in the real-time image data and second points in the previously-captured image data; and adjusting weights of the point-to-point correspondences based on the determination that the first points in the point-to-point correspondences likely correspond to the object of interest; and displaying the previously-captured image data over the object of interest in the 3D virtual view of the scene.

15. The method of claim 14 wherein the one or more characteristics include at least one of color information, angular information, and specular information.

16. The method of claim 14 wherein determining that the first portion of the real-time image data likely corresponds to the object of interest includes determining that the light-field image data corresponding to the first portion of the real-time image data has a lower saturation than other portions of the light-field image data.

\* \* \* \* \*